(12) United States Patent
Skerra et al.

(10) Patent No.: US 10,815,508 B2
(45) Date of Patent: Oct. 27, 2020

(54) ENZYMATIC METHOD FOR PRODUCING 2-HYDROXY-4-METHYLMERCAPTOBUTANOIC ACID (MHA)

(71) Applicant: Evonik Degussa GmbH, Essen (DE)

(72) Inventors: Arne Skerra, Dachau (DE); Julia Martin, Freising (DE); Harald Jakob, Hasselroth (DE); Daniel Fischer, Midlothian, VA (US)

(73) Assignee: Evonik Operations GmbH, Essen (DE)

( * ) Notice: Subject to any disclaimer, the term of this patent is extended or adjusted under 35 U.S.C. 154(b) by 312 days.

(21) Appl. No.: 15/947,824

(22) Filed: Apr. 8, 2018

(65) Prior Publication Data

US 2018/0298410 A1   Oct. 18, 2018

(30) Foreign Application Priority Data

Apr. 13, 2017  (EP) ..................................... 17166447

(51) Int. Cl.
| | |
|---|---|
| C12P 11/00 | (2006.01) |
| C12P 13/00 | (2006.01) |
| C12P 13/12 | (2006.01) |
| C12P 7/42 | (2006.01) |

(52) U.S. Cl.
CPC ................. *C12P 11/00* (2013.01); *C12P 7/42* (2013.01); *C12Y 101/01258* (2013.01); *C12Y 401/01001* (2013.01); *C12Y 401/01043* (2013.01); *C12Y 401/01072* (2013.01); *C12Y 101/01* (2013.01); *C12Y 117/01* (2013.01)

(58) Field of Classification Search
CPC ...................................................... C12P 11/00
See application file for complete search history.

(56) References Cited

U.S. PATENT DOCUMENTS

| | | |
|---|---|---|
| 4,782,173 A | 11/1988 | Burrington et al. |
| 5,847,207 A | 12/1998 | Suchsland et al. |
| 6,140,536 A | 10/2000 | Hasseberg et al. |
| 6,184,414 B1 | 2/2001 | Suchsland et al. |
| 6,475,370 B2 | 11/2002 | Lehmann et al. |
| 9,023,624 B2 | 5/2015 | Figge et al. |

FOREIGN PATENT DOCUMENTS

| | | |
|---|---|---|
| WO | WO 02/16671 | 2/2002 |
| WO | WO 2012/090022 | 7/2012 |
| WO | WO 2017/005910 | 1/2017 |
| WO | WO 2018/104143 | 6/2018 |

OTHER PUBLICATIONS

European Search Report and Opinion for corresponding European application EP 17 16 6447 dated Apr. 13, 2017.
Amárita, et al., "Conversion of methionine to methional by *Lactococcus lactis*," *FEMS Microbiology Letters* 204:189-195 (Oct. 2001).
Egorov, et al., "NAD-Dependent Formate Dehydrogenase from Methylotrophic Bacterium, Strain 1," *Eur. J. Biochem.* 99(3):569-576 (Sep. 1979).
Hummel, et al., "D-2-hydroxyisocaproate dehydrogenase from *Lactobacillus casei*," *Appl. Microbiol. Biotechnol.* 21:7-15 (Jan. 1985).
Ince, et al., "Ethylene formation by cell-free extracts of *Escherichia coli*," *Arch. Microbiol.* 146(2):151-158 (Nov. 1986).
Killenberg-Jabs, et al., "Role of Glu51 for Cofactor Binding and Catalytic Activity in Pyruvate Decarboxylase from Yeast Studied by Site-Directed Mutagenesis," *Biochemistry* 36(7):1900-1905 (Feb. 1997).
Kneen, et al., "Characterization of a thiamin diphosphate-dependent phenylpyruvate decarboxylase from *Saccharomyces cerevisiae*," *FEBS J.* 278(11):1842-1853 (Jun. 2011).
Miyazaki, et al., "Enzymatic synthesis of pyruvic acid from acetaldehyde and carbon dioxide," *Chemical Communications* 1800-1801 (2001).
Schütte, et al., "L-2-hydroxyisocaproate dehydrogenase—A new enzyme from *Lactobacillus confusus* for the sterospecific reduction of 2-ketocarboxylic acids," *Appl. Microbiol. Biotechnol.* 19(3):167-176 (Mar. 1984).
Schütte, et al., "Purification and Properties of Formaldehyde Dehydrogenase and Formate Dehydrogenase from *Candida boidinii*," *Eur. J. Biochem..* 62(1):151-160 (Feb. 1976).
Skerra, "Use of the tetracycline promoter for the tightly regulated production of a murine antibody fragment in *Escherichia coli*," *Gene* 151(1-2):131-135 (Dec. 1994).
Slusarczyk, et al., "Stabilization of NAD-dependent formate dehydrogenase from *Candida boidinii* by site-directed mutagensis of cysteine residues," *Eur. J. Biochem.* 267(5):1280-1289 (Mar. 2000).
Studier, et al., "Use of Bacteriophage T7 RNA Polymerase to Direct Selective High-level Expression of Cloned Genes," *J. Mol. Biol.* 189(1):113-130 (May 1986).
Tong, et al., "Enzymatic Synthesis of L-Lactic Acid From Carbon Dioxide and Ethanol With an Inherent Cofactor Regeneration Cycle," *Biotechnology and Bioengineering* 108(2):465-469 (Feb. 2011).
Wichmann, et al., "Continuous Enzymatic Transformation in an Enzyme Membrane Reactor with Simultaneous NAD(H) Regeneration," *Biotechnology and Bioengineering* 23(12):2789-2802 (Dec. 1981).
Yep, et al., "Determinants of substrate specificity in KdcA, a thiamin diphosphate-dependent decarboxylase," *Bioorganic Chemistry* 34(6):325-336 (Dec. 2006).

*Primary Examiner* — Maryam Monshipouri

(74) *Attorney, Agent, or Firm* — Law Office of: Michael A. Sanzo, LLC

(57) ABSTRACT

The invention relates to an enzymatic method for producing 2-hydroxy-4-methylmercaptobutanoic acid from 3-methyl-thio-propanal (3-methylmercaptopropanal (MMP) or "methional") and carbon dioxide.

20 Claims, 4 Drawing Sheets

Specification includes a Sequence Listing.

SEQUENCE LISTING

<160> NUMBER OF SEQ ID NOS: 14

<210> SEQ ID NO 1
<211> LENGTH: 1719
<212> TYPE: DNA
<213> ORGANISM: Saccharomyces cerevisiae
<220> FEATURE:
<221> NAME/KEY: misc_feature
<222> LOCATION: (1)..(6)

<223> OTHER INFORMATION: NdeI restriction site
<220> FEATURE:
<221> NAME/KEY: CDS
<222> LOCATION: (4)..(1719)
<223> OTHER INFORMATION: sequence of PDC1 from Sacharomyces cerevisiae
      optimized for the codon usage of Escherichia coli with a
      carboxy-terminal His6-tag
<220> FEATURE:
<221> NAME/KEY: misc_feature
<222> LOCATION: (1693)..(1698)
<223> OTHER INFORMATION: XhoI restriction site

<400> SEQUENCE: 1

```
cat atg agc gaa att acc ctg ggc aaa tac ctg ttt gaa cgc ctg aaa      48
    Met Ser Glu Ile Thr Leu Gly Lys Tyr Leu Phe Glu Arg Leu Lys
    1               5                   10                  15 cag gtt aat gtg aat acc gtt ttt ggt ctg cct ggc gat ttt aat ctg      96
Gln Val Asn Val Asn Thr Val Phe Gly Leu Pro Gly Asp Phe Asn Leu
                20                  25                  30 agc ctg ctg gat aaa atc tat gaa gtt gaa ggt atg cgt tgg gca ggt     144
Ser Leu Leu Asp Lys Ile Tyr Glu Val Glu Gly Met Arg Trp Ala Gly
            35                  40                  45 aat gca aat gaa ctg aat gca gcc tat gca gca gat ggt tat gca cgt     192
Asn Ala Asn Glu Leu Asn Ala Ala Tyr Ala Ala Asp Gly Tyr Ala Arg
        50                  55                  60 att aaa ggt atg agc tgc att att acc acc ttt ggt gtt ggt gaa ctg     240
Ile Lys Gly Met Ser Cys Ile Ile Thr Thr Phe Gly Val Gly Glu Leu
65                  70                  75 agc gca ctg aat ggt att gca ggt agc tat gca gaa cat gtt ggt gtg     288
Ser Ala Leu Asn Gly Ile Ala Gly Ser Tyr Ala Glu His Val Gly Val
80                  85                  90                  95 ctg cat gtt gtt ggt gtt ccg agc att agc gca cag gca aaa cag ctg     336
Leu His Val Val Gly Val Pro Ser Ile Ser Ala Gln Ala Lys Gln Leu
                100                 105                 110 ctg ctg cat cat acc ctg ggt aat ggt gat ttt acc gtg ttt cat cgt     384
Leu Leu His His Thr Leu Gly Asn Gly Asp Phe Thr Val Phe His Arg
            115                 120                 125 atg agc gca aat att agc gaa acc acc gca atg att acc gat att gca     432
Met Ser Ala Asn Ile Ser Glu Thr Thr Ala Met Ile Thr Asp Ile Ala
        130                 135                 140 acc gca ccg gca gaa att gat cgt tgt att cgt acc acc tat gtt acc     480
Thr Ala Pro Ala Glu Ile Asp Arg Cys Ile Arg Thr Thr Tyr Val Thr
145                 150                 155 cag cgt ccg gtt tat ctg ggt ctg cca gca aat ctg gtt gat ctg aat     528
Gln Arg Pro Val Tyr Leu Gly Leu Pro Ala Asn Leu Val Asp Leu Asn
160                 165                 170                 175 gtt ccg gct aaa ctg ctg caa acc ccg att gat atg agc ctg aaa ccg     576
Val Pro Ala Lys Leu Leu Gln Thr Pro Ile Asp Met Ser Leu Lys Pro
                180                 185                 190 aat gat gca gaa agc gaa aaa gaa gtg att gat acc att ctg gcc ctg     624
Asn Asp Ala Glu Ser Glu Lys Glu Val Ile Asp Thr Ile Leu Ala Leu
            195                 200                 205 gtt aaa gat gca aaa aat ccg gtt att ctg gca gat gcc tgt tgt agc     672
Val Lys Asp Ala Lys Asn Pro Val Ile Leu Ala Asp Ala Cys Cys Ser
        210                 215                 220 cgt cat gat gtt aaa gca gaa acc aaa aaa ctg atc gac ctg acc cag     720
Arg His Asp Val Lys Ala Glu Thr Lys Lys Leu Ile Asp Leu Thr Gln
225                 230                 235 ttt ccg gca ttt gtt acc ccg atg ggt aaa ggt agc att gat gaa cag     768
Phe Pro Ala Phe Val Thr Pro Met Gly Lys Gly Ser Ile Asp Glu Gln
240                 245                 250                 255 cat ccg cgt tat ggt ggt gtt tat gtt ggc acc ctg agc aaa ccg gaa     816
```

```
His Pro Arg Tyr Gly Gly Val Tyr Val Gly Thr Leu Ser Lys Pro Glu
                260                 265                 270 gtt aaa gaa gca gtt gaa agc gca gat ctg att ctg agc gtt ggt gca      864
Val Lys Glu Ala Val Glu Ser Ala Asp Leu Ile Leu Ser Val Gly Ala
            275                 280                 285 ctg ctg agt gat ttt aac acc ggt agc ttt tcg tat agc tac aaa acg      912
Leu Leu Ser Asp Phe Asn Thr Gly Ser Phe Ser Tyr Ser Tyr Lys Thr
            290                 295                 300 aaa aac atc gtc gag ttt cat agc gat cac atg aaa att cgt aat gca      960
Lys Asn Ile Val Glu Phe His Ser Asp His Met Lys Ile Arg Asn Ala
            305                 310                 315 acc ttt ccg ggt gtg cag atg aaa ttt gtt ctg caa aaa ctg ctg acc     1008
Thr Phe Pro Gly Val Gln Met Lys Phe Val Leu Gln Lys Leu Leu Thr
320                 325                 330                 335 acc att gca gat gca gca aaa ggt tat aaa ccg gtt gca gtt ccg gca     1056
Thr Ile Ala Asp Ala Ala Lys Gly Tyr Lys Pro Val Ala Val Pro Ala
            340                 345                 350 cgt aca ccg gca aat gca gcc gtt ccg gca tca aca ccg ctg aaa caa     1104
Arg Thr Pro Ala Asn Ala Ala Val Pro Ala Ser Thr Pro Leu Lys Gln
            355                 360                 365 gaa tgg atg tgg aat cag ctg ggt aat ttt ctg caa gag ggt gat gtt     1152
Glu Trp Met Trp Asn Gln Leu Gly Asn Phe Leu Gln Glu Gly Asp Val
            370                 375                 380 gtt att gca gaa acc ggc acc agc gca ttt ggt att aat cag acc acc     1200
Val Ile Ala Glu Thr Gly Thr Ser Ala Phe Gly Ile Asn Gln Thr Thr
385                 390                 395 ttt ccg aat aac acc tat ggt att agc cag gtt ctg tgg ggt agt att     1248
Phe Pro Asn Asn Thr Tyr Gly Ile Ser Gln Val Leu Trp Gly Ser Ile
400                 405                 410                 415 ggt ttt acc acc ggt gca acc ctg ggt gca gca ttt gca gcc gaa gaa     1296
Gly Phe Thr Thr Gly Ala Thr Leu Gly Ala Ala Phe Ala Ala Glu Glu
            420                 425                 430 atc gat ccg aaa aaa cgt gtg att ctg ttt att ggt gat ggt agc ctg     1344
Ile Asp Pro Lys Lys Arg Val Ile Leu Phe Ile Gly Asp Gly Ser Leu
            435                 440                 445 caa ctg acc gtt caa gaa att agc acc atg att cgt tgg ggt ctg aaa     1392
Gln Leu Thr Val Gln Glu Ile Ser Thr Met Ile Arg Trp Gly Leu Lys
            450                 455                 460 ccg tac ctg ttc gtt ctg aat aat gat ggc tat acc atc gag aaa ctg     1440
Pro Tyr Leu Phe Val Leu Asn Asn Asp Gly Tyr Thr Ile Glu Lys Leu
465                 470                 475 atc cac ggt ccg aaa gca cag tat aat gaa att cag ggt tgg gat cat     1488
Ile His Gly Pro Lys Ala Gln Tyr Asn Glu Ile Gln Gly Trp Asp His
480                 485                 490                 495 ctg tca ctg ctg ccg acc ttt ggc gca aaa gat tat gaa aca cat cgt     1536
Leu Ser Leu Leu Pro Thr Phe Gly Ala Lys Asp Tyr Glu Thr His Arg
            500                 505                 510 gtt gca acc aca ggt gaa tgg gat aaa ctg acc cag gat aaa tcc ttt     1584
Val Ala Thr Thr Gly Glu Trp Asp Lys Leu Thr Gln Asp Lys Ser Phe
            515                 520                 525 aat gat aac agc aaa atc cgc atg atc gaa att atg ctg ccg gtt ttt     1632
Asn Asp Asn Ser Lys Ile Arg Met Ile Glu Ile Met Leu Pro Val Phe
            530                 535                 540 gat gca ccg cag aat ctg gtg gaa cag gcc aaa ctg acc gca gca acc     1680
Asp Ala Pro Gln Asn Leu Val Glu Gln Ala Lys Leu Thr Ala Ala Thr
            545                 550                 555 aat gca aaa cag ctc gag cac cac cac cac cac cac tga                 1719
Asn Ala Lys Gln Leu Glu His His His His His His
560                 565                 570
```

-continued

<210> SEQ ID NO 2
<211> LENGTH: 571
<212> TYPE: PRT
<213> ORGANISM: Saccharomyces cerevisiae

<400> SEQUENCE: 2

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

-continued

```
Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
            405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
            485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln Leu Glu His His His His His His
            565                 570
```

```
<210> SEQ ID NO 3
<211> LENGTH: 1932
<212> TYPE: DNA
<213> ORGANISM: Saccharomyces cerevisiae
<220> FEATURE:
<221> NAME/KEY: misc_feature
<222> LOCATION: (1)..(6)
<223> OTHER INFORMATION: NdeI restriction site
<220> FEATURE:
<221> NAME/KEY: CDS
<222> LOCATION: (4)..(1932)
<223> OTHER INFORMATION: sequence of ARO10 of Sacharomyces cerevisiae
      optimized for the codon usage of Escherichia coli with a
      carboxy-terminal His6-tag
<220> FEATURE:
<221> NAME/KEY: misc_feature
<222> LOCATION: (1906)..(1911)
<223> OTHER INFORMATION: XhoI restriction site

<400> SEQUENCE: 3 cat atg gca ccg gtt acc att gaa aaa ttc gtg aat caa gaa gaa cgc    48
    Met Ala Pro Val Thr Ile Glu Lys Phe Val Asn Gln Glu Glu Arg
    1               5                  10                  15 cac ctg gtt agc aat cgt agc gca acc att ccg ttt ggt gaa tat atc    96
His Leu Val Ser Asn Arg Ser Ala Thr Ile Pro Phe Gly Glu Tyr Ile
            20                  25                  30 ttt aaa cgc ctg ctg agc att gat acc aaa agc gtg ttt ggt gtt ccg   144
Phe Lys Arg Leu Leu Ser Ile Asp Thr Lys Ser Val Phe Gly Val Pro
        35                  40                  45 ggt gat ttt aat ctg agc ctg ctg gaa tat ctg tat agc ccg agc gtt   192
Gly Asp Phe Asn Leu Ser Leu Leu Glu Tyr Leu Tyr Ser Pro Ser Val
    50                  55                  60 gaa agc gca ggt ctg cgt tgg gtt ggc acc tgt aat gaa ctg aat gca   240
Glu Ser Ala Gly Leu Arg Trp Val Gly Thr Cys Asn Glu Leu Asn Ala
65                  70                  75
```

```
gcc tat gca gca gat ggt tat agc cgt tat agc aac aaa att ggt tgt      288
Ala Tyr Ala Ala Asp Gly Tyr Ser Arg Tyr Ser Asn Lys Ile Gly Cys
 80              85                  90                  95 ctg att acc acc tat ggt gtt ggt gaa ctg agc gca ctg aat ggt att      336
Leu Ile Thr Thr Tyr Gly Val Gly Glu Leu Ser Ala Leu Asn Gly Ile
                100                 105                 110 gca ggt agc ttt gca gaa aat gtg aaa gtg ctg cat att gtt ggt gtg      384
Ala Gly Ser Phe Ala Glu Asn Val Lys Val Leu His Ile Val Gly Val
            115                 120                 125 gcc aaa agt att gat agc cgt agc agc aat ttt agc gat cgt aat ctg      432
Ala Lys Ser Ile Asp Ser Arg Ser Ser Asn Phe Ser Asp Arg Asn Leu
        130                 135                 140 cat cat ctg gtt ccg cag ctg cat gat agc aac ttt aaa ggt ccg aac      480
His His Leu Val Pro Gln Leu His Asp Ser Asn Phe Lys Gly Pro Asn
    145                 150                 155 cat aaa gtg tat cac gac atg gtt aaa gat cgt gtt gca tgt agc gtt      528
His Lys Val Tyr His Asp Met Val Lys Asp Arg Val Ala Cys Ser Val
160                 165                 170                 175 gca tat ctg gaa gat att gaa acc gca tgt gat cag gtg gat aat gtg      576
Ala Tyr Leu Glu Asp Ile Glu Thr Ala Cys Asp Gln Val Asp Asn Val
                180                 185                 190 att cgc gat atc tat aaa tac agc aaa ccg ggt tat atc ttt gtg cct      624
Ile Arg Asp Ile Tyr Lys Tyr Ser Lys Pro Gly Tyr Ile Phe Val Pro
            195                 200                 205 gcc gat ttt gca gat atg agc gtt acc tgt gat aat ctg gtt aat gtt      672
Ala Asp Phe Ala Asp Met Ser Val Thr Cys Asp Asn Leu Val Asn Val
        210                 215                 220 ccg cgt att agc cag cag gat tgt att gtt tat ccg agc gaa aat cag      720
Pro Arg Ile Ser Gln Gln Asp Cys Ile Val Tyr Pro Ser Glu Asn Gln
    225                 230                 235 ctg agc gac att att aac aaa atc acc agc tgg atc tat agc agc aaa      768
Leu Ser Asp Ile Ile Asn Lys Ile Thr Ser Trp Ile Tyr Ser Ser Lys
240                 245                 250                 255 aca ccg gca att ctg ggt gat gtt ctg acc gat cgt tat ggt gtt agc      816
Thr Pro Ala Ile Leu Gly Asp Val Leu Thr Asp Arg Tyr Gly Val Ser
                260                 265                 270 aat ttt ctg aac aaa ctg att tgc aaa acc ggc atc tgg aat ttt tct      864
Asn Phe Leu Asn Lys Leu Ile Cys Lys Thr Gly Ile Trp Asn Phe Ser
            275                 280                 285 acc gtt atg ggt aaa agc gtg atc gat gaa agc aat ccg acc tat atg      912
Thr Val Met Gly Lys Ser Val Ile Asp Glu Ser Asn Pro Thr Tyr Met
        290                 295                 300 ggt cag tat aat ggt aaa gaa ggc ctg aaa cag gtc tat gaa cat ttt      960
Gly Gln Tyr Asn Gly Lys Glu Gly Leu Lys Gln Val Tyr Glu His Phe
    305                 310                 315 gaa ctg tgt gat ctg gtg ctg cat ttt ggc gtt gac att aac gaa att     1008
Glu Leu Cys Asp Leu Val Leu His Phe Gly Val Asp Ile Asn Glu Ile
320                 325                 330                 335 aac aac ggc cat tac acc ttc acc tat aaa ccg aat gca aaa atc atc     1056
Asn Asn Gly His Tyr Thr Phe Thr Tyr Lys Pro Asn Ala Lys Ile Ile
                340                 345                 350 cag ttc cac ccg aac tat att cgt ctg gtt gat acc cgt cag ggt aat     1104
Gln Phe His Pro Asn Tyr Ile Arg Leu Val Asp Thr Arg Gln Gly Asn
            355                 360                 365 gag cag atg ttt aaa ggt att aac ttt gca ccg atc ctg aaa gag ctg     1152
Glu Gln Met Phe Lys Gly Ile Asn Phe Ala Pro Ile Leu Lys Glu Leu
        370                 375                 380 tat aaa cgt att gat gtg agc aaa ctg tcc ctg caa tat gat agt aat     1200
Tyr Lys Arg Ile Asp Val Ser Lys Leu Ser Leu Gln Tyr Asp Ser Asn
    385                 390                 395
```

```
gtt acc cag tat acc aac gaa acc atg cgc ctg gaa gat ccg acc aat    1248
Val Thr Gln Tyr Thr Asn Glu Thr Met Arg Leu Glu Asp Pro Thr Asn
400                 405                 410                 415 ggt cag agc agc att att acc cag gtt cat ctg caa aaa acg atg ccg    1296
Gly Gln Ser Ser Ile Ile Thr Gln Val His Leu Gln Lys Thr Met Pro
            420                 425                 430 aaa ttt ctg aat cca ggt gat gtt gtt gtt tgt gaa acc ggt agc ttt    1344
Lys Phe Leu Asn Pro Gly Asp Val Val Val Cys Glu Thr Gly Ser Phe
    435                 440                 445 cag ttt agc gtt cgt gat ttt gca ttt ccg agc cag ctg aaa tat atc    1392
Gln Phe Ser Val Arg Asp Phe Ala Phe Pro Ser Gln Leu Lys Tyr Ile
450                 455                 460 agc cag ggt ttt ttt ctg agt att ggt atg gca ctg cct gcc gca ctg    1440
Ser Gln Gly Phe Phe Leu Ser Ile Gly Met Ala Leu Pro Ala Ala Leu
465                 470                 475 ggt gtt ggt atc gca atg cag gat cat agc aat gca cat att aat ggt    1488
Gly Val Gly Ile Ala Met Gln Asp His Ser Asn Ala His Ile Asn Gly
480                 485                 490                 495 ggc aac gtg aaa gag gat tat aaa ccg cgt ctg att ctg ttt gaa ggt    1536
Gly Asn Val Lys Glu Asp Tyr Lys Pro Arg Leu Ile Leu Phe Glu Gly
            500                 505                 510 gat ggt gca gca cag atg acc att caa gaa ctg agc acc att ctg aaa    1584
Asp Gly Ala Ala Gln Met Thr Ile Gln Glu Leu Ser Thr Ile Leu Lys
    515                 520                 525 tgt aat att ccg ctg gaa gtg atc atc tgg aac aat aat ggt tat acg    1632
Cys Asn Ile Pro Leu Glu Val Ile Ile Trp Asn Asn Asn Gly Tyr Thr
530                 535                 540 att gag cgt gca att atg ggt ccg acc cgt agc tat aat gat gtt atg    1680
Ile Glu Arg Ala Ile Met Gly Pro Thr Arg Ser Tyr Asn Asp Val Met
545                 550                 555 agc tgg aaa tgg acc aaa ctg ttt gag gca ttt ggc gat ttt gat ggc    1728
Ser Trp Lys Trp Thr Lys Leu Phe Glu Ala Phe Gly Asp Phe Asp Gly
560                 565                 570                 575 aaa tat acc aat agc acc ctg att cag tgt ccg agt aaa ctg gca ctg    1776
Lys Tyr Thr Asn Ser Thr Leu Ile Gln Cys Pro Ser Lys Leu Ala Leu
            580                 585                 590 aaa ctg gaa gaa ctg aaa aac agc aat aaa cgc agc ggt att gaa ctg    1824
Lys Leu Glu Glu Leu Lys Asn Ser Asn Lys Arg Ser Gly Ile Glu Leu
    595                 600                 605 ctg gaa gtt aaa ctg ggc gaa ctg gat ttt ccg gaa caa ctg aaa tgc    1872
Leu Glu Val Lys Leu Gly Glu Leu Asp Phe Pro Glu Gln Leu Lys Cys
610                 615                 620 atg gtt gaa gca gca gcc ctg aaa cgt aat aaa ctc gag cac cac cac    1920
Met Val Glu Ala Ala Ala Leu Lys Arg Asn Lys Leu Glu His His His
625                 630                 635 cac cac cac tga                                                    1932
His His His
640
```

<210> SEQ ID NO 4
<211> LENGTH: 642
<212> TYPE: PRT
<213> ORGANISM: Saccharomyces cerevisiae

<400> SEQUENCE: 4

```
Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30
```

```
Lys Arg Leu Leu Ser Ile Asp Thr Lys Ser Val Phe Gly Val Pro Gly
             35                  40                  45

Asp Phe Asn Leu Ser Leu Leu Glu Tyr Leu Tyr Ser Pro Ser Val Glu
 50                  55                  60

Ser Ala Gly Leu Arg Trp Val Gly Thr Cys Asn Glu Leu Asn Ala Ala
 65                  70                  75                  80

Tyr Ala Ala Asp Gly Tyr Ser Arg Tyr Ser Asn Lys Ile Gly Cys Leu
                 85                  90                  95

Ile Thr Thr Tyr Gly Val Gly Glu Leu Ser Ala Leu Asn Gly Ile Ala
                100                 105                 110

Gly Ser Phe Ala Glu Asn Val Lys Val Leu His Ile Val Gly Val Ala
            115                 120                 125

Lys Ser Ile Asp Ser Arg Ser Ser Asn Phe Ser Asp Arg Asn Leu His
130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
            195                 200                 205

Asp Phe Ala Asp Met Ser Val Thr Cys Asp Asn Leu Val Asn Val Pro
        210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
        370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
                405                 410                 415

Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
        435                 440                 445

Phe Ser Val Arg Asp Phe Ala Phe Pro Ser Gln Leu Lys Tyr Ile Ser
```

```
                450              455              460
Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
        515                 520                 525

Asn Ile Pro Leu Glu Val Ile Ile Trp Asn Asn Asn Gly Tyr Thr Ile
    530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
        595                 600                 605

Glu Val Lys Leu Gly Glu Leu Asp Phe Pro Glu Gln Leu Lys Cys Met
    610                 615                 620

Val Glu Ala Ala Leu Lys Arg Asn Lys Leu Glu His His His His
625                 630                 635                 640

His His
```

<210> SEQ ID NO 5
<211> LENGTH: 1671
<212> TYPE: DNA
<213> ORGANISM: Lactococcus lactis
<220> FEATURE:
<221> NAME/KEY: misc_feature
<222> LOCATION: (1)..(6)
<223> OTHER INFORMATION: NdeI restriction site
<220> FEATURE:
<221> NAME/KEY: CDS
<222> LOCATION: (4)..(1671)
<223> OTHER INFORMATION: sequence of kdcA from Lactococcus lactis
    optimized for the codon usage of Escherichia coli with a
    carboxy-terminal His6-tag
<220> FEATURE:
<221> NAME/KEY: misc_feature
<222> LOCATION: (1645)..(1650)
<223> OTHER INFORMATION: XhoI restriction site

<400> SEQUENCE: 5

```
cat atg tat acc gtt ggt gat tat ctg ctg gat cgt ctg cat gaa ctg      48
    Met Tyr Thr Val Gly Asp Tyr Leu Leu Asp Arg Leu His Glu Leu
    1               5                  10                  15 ggt att gaa gaa att ttt ggt gtt ccg ggt gat tac aac ctg caa ttt      96
Gly Ile Glu Glu Ile Phe Gly Val Pro Gly Asp Tyr Asn Leu Gln Phe
            20                  25                  30 ctg gat cag att atc agc cgt gaa gat atg aaa tgg att ggc aat gcg     144
Leu Asp Gln Ile Ile Ser Arg Glu Asp Met Lys Trp Ile Gly Asn Ala
        35                  40                  45 aat gaa ctg aat gca agc tat atg gca gat ggt tat gca cgt acc aaa     192
Asn Glu Leu Asn Ala Ser Tyr Met Ala Asp Gly Tyr Ala Arg Thr Lys
    50                  55                  60 aaa gca gca gca ttt ctg acc acc ttt ggt gtt ggt gaa ctg agc gca     240
Lys Ala Ala Ala Phe Leu Thr Thr Phe Gly Val Gly Glu Leu Ser Ala
65                  70                  75
```

```
att aat ggt ctg gca ggt agc tat gca gaa aat ctg ccg gtt gtt gaa      288
Ile Asn Gly Leu Ala Gly Ser Tyr Ala Glu Asn Leu Pro Val Val Glu
80              85                  90                  95 att gtt ggt agc ccg acc agc aaa gtt cag aat gat ggt aaa ttt gtg      336
Ile Val Gly Ser Pro Thr Ser Lys Val Gln Asn Asp Gly Lys Phe Val
            100                 105                 110 cat cat acc ctg gcc gat ggt gat ttt aaa cac ttt atg aaa atg cac      384
His His Thr Leu Ala Asp Gly Asp Phe Lys His Phe Met Lys Met His
        115                 120                 125 gaa ccg gtt acc gca gca cgt acc ctg ctg acc gca gaa aat gca acc      432
Glu Pro Val Thr Ala Ala Arg Thr Leu Leu Thr Ala Glu Asn Ala Thr
        130                 135                 140 tat gaa att gat cgt gtt ctg agc cag ctg ctg aaa gaa cgt aaa ccg      480
Tyr Glu Ile Asp Arg Val Leu Ser Gln Leu Leu Lys Glu Arg Lys Pro
145                 150                 155 gtg tat att aac ctg ccg gtg gat gtt gca gca gca aaa gca gaa aaa      528
Val Tyr Ile Asn Leu Pro Val Asp Val Ala Ala Ala Lys Ala Glu Lys
160                 165                 170                 175 ccg gca ctg agc ctg gaa aaa gaa agc agc acc acc aat acc acc gaa      576
Pro Ala Leu Ser Leu Glu Lys Glu Ser Ser Thr Thr Asn Thr Thr Glu
            180                 185                 190 cag gtt att ctg agc aaa atc gaa gaa agc ctg aaa aat gcc cag aaa      624
Gln Val Ile Leu Ser Lys Ile Glu Glu Ser Leu Lys Asn Ala Gln Lys
        195                 200                 205 ccg gtt gtt att gca ggt cat gaa gtt att agc ttt ggg ctg gaa aaa      672
Pro Val Val Ile Ala Gly His Glu Val Ile Ser Phe Gly Leu Glu Lys
        210                 215                 220 acc gtt acc cag ttt gtt agc gaa acc aaa ctg ccg att acc acc ctg      720
Thr Val Thr Gln Phe Val Ser Glu Thr Lys Leu Pro Ile Thr Thr Leu
225                 230                 235 aat ttt ggt aaa agc gca gtt gat gaa agc ctg ccg agc ttt ctg ggt      768
Asn Phe Gly Lys Ser Ala Val Asp Glu Ser Leu Pro Ser Phe Leu Gly
240                 245                 250                 255 atc tat aat ggt aaa ctg tcc gag atc tcc ctg aaa aac ttt gtt gaa      816
Ile Tyr Asn Gly Lys Leu Ser Glu Ile Ser Leu Lys Asn Phe Val Glu
            260                 265                 270 agc gca gat ttc att ctg atg ctg ggt gtt aaa ctg acc gat agc agt      864
Ser Ala Asp Phe Ile Leu Met Leu Gly Val Lys Leu Thr Asp Ser Ser
        275                 280                 285 acc ggt gca ttt acc cat cat ctg gat gaa aac aaa atg atc agc ctg      912
Thr Gly Ala Phe Thr His His Leu Asp Glu Asn Lys Met Ile Ser Leu
        290                 295                 300 aac att gat gag ggc atc atc ttt aac aaa gtg gtg gaa gat ttt gat      960
Asn Ile Asp Glu Gly Ile Ile Phe Asn Lys Val Val Glu Asp Phe Asp
305                 310                 315 ttt cgt gca gtt gtt agc agc ctg agc gaa ctg aaa ggt att gaa tat     1008
Phe Arg Ala Val Val Ser Ser Leu Ser Glu Leu Lys Gly Ile Glu Tyr
320                 325                 330                 335 gaa ggc cag tac atc gac aaa cag tat gaa gaa ttt att ccg agc agc     1056
Glu Gly Gln Tyr Ile Asp Lys Gln Tyr Glu Glu Phe Ile Pro Ser Ser
            340                 345                 350 gca ccg ctg agc cag gat cgc ctg tgg cag gca gtt gaa agt ctg acc     1104
Ala Pro Leu Ser Gln Asp Arg Leu Trp Gln Ala Val Glu Ser Leu Thr
        355                 360                 365 cag agc aat gaa acc att gtt gca gaa cag ggc acc agt ttt ttt ggt     1152
Gln Ser Asn Glu Thr Ile Val Ala Glu Gln Gly Thr Ser Phe Phe Gly
        370                 375                 380 gca agc acc att ttt ctg aaa agc aac agc cgt ttt att ggt cag ccg     1200
Ala Ser Thr Ile Phe Leu Lys Ser Asn Ser Arg Phe Ile Gly Gln Pro
385                 390                 395
```

```
ctg tgg ggt agc att ggt tat acc ttt ccg gca gca ctg ggt agc cag    1248
Leu Trp Gly Ser Ile Gly Tyr Thr Phe Pro Ala Ala Leu Gly Ser Gln
400             405                 410                 415 att gca gat aaa gaa agc cgt cat ctg ctg ttt att ggt gat ggt agc    1296
Ile Ala Asp Lys Glu Ser Arg His Leu Leu Phe Ile Gly Asp Gly Ser
                420                 425                 430 ctg caa ctg acc gtt caa gaa ctg ggt ctg agc att cgt gaa aaa ctg    1344
Leu Gln Leu Thr Val Gln Glu Leu Gly Leu Ser Ile Arg Glu Lys Leu
            435                 440                 445 aat ccg att tgc ttc atc att aac aac gat ggc tat acc gtg gaa cgt    1392
Asn Pro Ile Cys Phe Ile Ile Asn Asn Asp Gly Tyr Thr Val Glu Arg
        450                 455                 460 gaa att cat ggt ccg acc cag agt tat aat gat att ccg atg tgg aac    1440
Glu Ile His Gly Pro Thr Gln Ser Tyr Asn Asp Ile Pro Met Trp Asn
465                 470                 475 tac tcg aaa ctg cct gaa acc ttt ggc gca acc gaa gat cgt gtg gtt    1488
Tyr Ser Lys Leu Pro Glu Thr Phe Gly Ala Thr Glu Asp Arg Val Val
480                 485                 490                 495 agc aaa att gtt cgt acc gaa aat gaa ttt gtg agc gtg atg aaa gaa    1536
Ser Lys Ile Val Arg Thr Glu Asn Glu Phe Val Ser Val Met Lys Glu
                500                 505                 510 gca cag gca gac gtt aat cgt atg tat tgg att gaa ctg gtg ctg gaa    1584
Ala Gln Ala Asp Val Asn Arg Met Tyr Trp Ile Glu Leu Val Leu Glu
            515                 520                 525 aaa gag gat gca ccg aaa ctg ctg aaa aaa atg ggt aaa ctg ttt gcc    1632
Lys Glu Asp Ala Pro Lys Leu Leu Lys Lys Met Gly Lys Leu Phe Ala
        530                 535                 540 gag cag aat aaa ctc gag cac cac cac cac cac cac tga                1671
Glu Gln Asn Lys Leu Glu His His His His His His
545                 550                 555
```

<210> SEQ ID NO 6
<211> LENGTH: 555
<212> TYPE: PRT
<213> ORGANISM: Lactococcus lactis

<400> SEQUENCE: 6

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160
```

Tyr Ile Asn Leu Pro Val Asp Val Ala Ala Ala Lys Ala Glu Lys Pro
             165                 170                 175

Ala Leu Ser Leu Glu Lys Glu Ser Ser Thr Asn Thr Thr Glu Gln
        180                 185                 190

Val Ile Leu Ser Lys Ile Glu Glu Ser Leu Lys Asn Ala Gln Lys Pro
            195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
    370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ser Ile Arg Glu Lys Leu Asn
    435                 440                 445

Pro Ile Cys Phe Ile Ile Asn Asn Asp Gly Tyr Thr Val Glu Arg Glu
450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
        500                 505                 510

Gln Ala Asp Val Asn Arg Met Tyr Trp Ile Glu Leu Val Leu Glu Lys
    515                 520                 525

Glu Asp Ala Pro Lys Leu Leu Lys Lys Met Gly Lys Leu Phe Ala Glu
530                 535                 540

Gln Asn Lys Leu Glu His His His His His
545                 550                 555

<210> SEQ ID NO 7
<211> LENGTH: 1048
<212> TYPE: DNA

<213> ORGANISM: Lactobacillus casei
<220> FEATURE:
<221> NAME/KEY: CDS
<222> LOCATION: (1)..(1044)
<223> OTHER INFORMATION: sequence of D-HicDH from Lactobacillus casei
    optimized for the codon usage of Escherichia coli with an
    amino-terminal His6-tag
<220> FEATURE:
<221> NAME/KEY: misc_feature
<222> LOCATION: (37)..(42)
<223> OTHER INFORMATION: KasI restriction site
<220> FEATURE:
<221> NAME/KEY: misc_feature
<222> LOCATION: (1043)..(1048)
<223> OTHER INFORMATION: HindIII restriction site

<400> SEQUENCE: 7

```
atg gct agc aga gga tcg cat cac cat cac cat cac ggc gcc atg aaa       48
Met Ala Ser Arg Gly Ser His His His His His His Gly Ala Met Lys
1               5                   10                  15 att atc gcc tat ggt gca cgt gtt gat gag atc cag tat ttc aaa cag       96
Ile Ile Ala Tyr Gly Ala Arg Val Asp Glu Ile Gln Tyr Phe Lys Gln
                20                  25                  30 tgg gca aaa gat acc ggt aac acc ctg gaa tat cat acc gaa ttt ctg      144
Trp Ala Lys Asp Thr Gly Asn Thr Leu Glu Tyr His Thr Glu Phe Leu
            35                  40                  45 gat gaa aat acc gtg gaa tgg gcc aaa ggt ttt gat ggt att aat agc      192
Asp Glu Asn Thr Val Glu Trp Ala Lys Gly Phe Asp Gly Ile Asn Ser
        50                  55                  60 ctg cag acc acc ccg tat gca gcc ggt gtt ttt gaa aaa atg cat gcc      240
Leu Gln Thr Thr Pro Tyr Ala Ala Gly Val Phe Glu Lys Met His Ala
65                  70                  75                  80 tat ggc atc aaa ttt ctg acc att cgt aat gtg ggc acc gat aat att      288
Tyr Gly Ile Lys Phe Leu Thr Ile Arg Asn Val Gly Thr Asp Asn Ile
                85                  90                  95 gat atg acc gca atg aaa cag tat ggt att cgt ctg agc aat gtt ccg      336
Asp Met Thr Ala Met Lys Gln Tyr Gly Ile Arg Leu Ser Asn Val Pro
                100                 105                 110 gca tat agt ccg gca gca att gca gaa ttt gca ctg acc gat acc ctg      384
Ala Tyr Ser Pro Ala Ala Ile Ala Glu Phe Ala Leu Thr Asp Thr Leu
            115                 120                 125 tat ctg ctg cgt aat atg ggt aaa gtt cag gca cag ctg cag gca ggc      432
Tyr Leu Leu Arg Asn Met Gly Lys Val Gln Ala Gln Leu Gln Ala Gly
        130                 135                 140 gat tat gaa aaa gca ggc acc ttt att ggt aaa gaa ctg ggt cag cag      480
Asp Tyr Glu Lys Ala Gly Thr Phe Ile Gly Lys Glu Leu Gly Gln Gln
145                 150                 155                 160 acc gtt ggt gtt atg ggc aca ggt cat att ggt cag gtt gca atc aaa      528
Thr Val Gly Val Met Gly Thr Gly His Ile Gly Gln Val Ala Ile Lys
                165                 170                 175 ctg ttt aaa ggc ttt ggt gcc aaa gtg att gcc tat gat ccg tat ccg      576
Leu Phe Lys Gly Phe Gly Ala Lys Val Ile Ala Tyr Asp Pro Tyr Pro
                180                 185                 190 atg aaa ggt gat cat ccg gat ttt gat tat gtt agc ctg gaa gac ctg      624
Met Lys Gly Asp His Pro Asp Phe Asp Tyr Val Ser Leu Glu Asp Leu
            195                 200                 205 ttc aaa cag agt gat gtt att gat ctg cat gtt ccg ggt att gaa cag      672
Phe Lys Gln Ser Asp Val Ile Asp Leu His Val Pro Gly Ile Glu Gln
        210                 215                 220 aac acc cat atc att aac gaa gca gcc ttt aat ctg atg aaa ccg ggt      720
Asn Thr His Ile Ile Asn Glu Ala Ala Phe Asn Leu Met Lys Pro Gly
225                 230                 235                 240 gca att gtg att aat acc gca cgt ccg aat ctg att gat acc cag gca      768
Ala Ile Val Ile Asn Thr Ala Arg Pro Asn Leu Ile Asp Thr Gln Ala
```

```
Ala Ile Val Ile Asn Thr Ala Arg Pro Asn Leu Ile Asp Thr Gln Ala
                    245                 250                 255 atg ctg agc aat ctg aaa agc ggt aaa ctg gca ggc gtt ggt att gat        816
Met Leu Ser Asn Leu Lys Ser Gly Lys Leu Ala Gly Val Gly Ile Asp
                260                 265                 270 acc tat gaa tat gaa acc gag gat ctg ctg aat ctg gca aaa cat ggt        864
Thr Tyr Glu Tyr Glu Thr Glu Asp Leu Leu Asn Leu Ala Lys His Gly
            275                 280                 285 agc ttt aaa gat ccg ctg tgg gat gaa ctg ctg ggt atg ccg aat gtt        912
Ser Phe Lys Asp Pro Leu Trp Asp Glu Leu Leu Gly Met Pro Asn Val
        290                 295                 300 gtt ctg agt ccg cat att gca tat tat acc gaa acc gca gtt cac aac        960
Val Leu Ser Pro His Ile Ala Tyr Tyr Thr Glu Thr Ala Val His Asn
305                 310                 315                 320 atg gtg tat ttt agt ctg cag cat ctg gtt gac ttt ctg aca aaa ggt       1008
Met Val Tyr Phe Ser Leu Gln His Leu Val Asp Phe Leu Thr Lys Gly
                325                 330                 335 gaa acc agc acc gaa gtt acc ggt ccg gca aaa taa gctt                  1048
Glu Thr Ser Thr Glu Val Thr Gly Pro Ala Lys
                340                 345

<210> SEQ ID NO 8
<211> LENGTH: 347
<212> TYPE: PRT
<213> ORGANISM: Lactobacillus casei

<400> SEQUENCE: 8

Met Ala Ser Arg Gly Ser His His His His His Gly Ala Met Lys
1               5                   10                  15

Ile Ile Ala Tyr Gly Ala Arg Val Asp Glu Ile Gln Tyr Phe Lys Gln
            20                  25                  30

Trp Ala Lys Asp Thr Gly Asn Thr Leu Glu Tyr His Thr Glu Phe Leu
        35                  40                  45

Asp Glu Asn Thr Val Glu Trp Ala Lys Gly Phe Asp Gly Ile Asn Ser
    50                  55                  60

Leu Gln Thr Thr Pro Tyr Ala Ala Gly Val Phe Glu Lys Met His Ala
65                  70                  75                  80

Tyr Gly Ile Lys Phe Leu Thr Ile Arg Asn Val Gly Thr Asp Asn Ile
                85                  90                  95

Asp Met Thr Ala Met Lys Gln Tyr Gly Ile Arg Leu Ser Asn Val Pro
            100                 105                 110

Ala Tyr Ser Pro Ala Ala Ile Ala Glu Phe Ala Leu Thr Asp Thr Leu
        115                 120                 125

Tyr Leu Leu Arg Asn Met Gly Lys Val Gln Ala Gln Leu Gln Ala Gly
    130                 135                 140

Asp Tyr Glu Lys Ala Gly Thr Phe Ile Gly Lys Glu Leu Gly Gln Gln
145                 150                 155                 160

Thr Val Gly Val Met Gly Thr Gly His Ile Gly Gln Val Ala Ile Lys
                165                 170                 175

Leu Phe Lys Gly Phe Gly Ala Lys Val Ile Ala Tyr Asp Pro Tyr Pro
            180                 185                 190

Met Lys Gly Asp His Pro Asp Phe Asp Tyr Val Ser Leu Glu Asp Leu
        195                 200                 205

Phe Lys Gln Ser Asp Val Ile Asp Leu His Val Pro Gly Ile Glu Gln
    210                 215                 220

Asn Thr His Ile Ile Asn Glu Ala Ala Phe Asn Leu Met Lys Pro Gly
225                 230                 235                 240
```

```
Ala Ile Val Ile Asn Thr Ala Arg Pro Asn Leu Ile Asp Thr Gln Ala
            245                 250                 255

Met Leu Ser Asn Leu Lys Ser Gly Lys Leu Ala Gly Val Gly Ile Asp
            260                 265                 270

Thr Tyr Glu Tyr Glu Thr Glu Asp Leu Leu Asn Leu Ala Lys His Gly
            275                 280                 285

Ser Phe Lys Asp Pro Leu Trp Asp Glu Leu Leu Gly Met Pro Asn Val
290                 295                 300

Val Leu Ser Pro His Ile Ala Tyr Tyr Thr Glu Thr Ala Val His Asn
305                 310                 315                 320

Met Val Tyr Phe Ser Leu Gln His Leu Val Asp Phe Leu Thr Lys Gly
            325                 330                 335

Glu Thr Ser Thr Glu Val Thr Gly Pro Ala Lys
            340                 345

<210> SEQ ID NO 9
<211> LENGTH: 960
<212> TYPE: DNA
<213> ORGANISM: Lactobacillus confuses
<220> FEATURE:
<221> NAME/KEY: misc_feature
<222> LOCATION: (1)..(6)
<223> OTHER INFORMATION: NdeI restriction site
<220> FEATURE:
<221> NAME/KEY: CDS
<222> LOCATION: (4)..(960)
<223> OTHER INFORMATION: sequence of L-HicDH from Lactobacillus confuses
      optimized for the codon usage of Escherichia coli with a
      carboxy-terminal His6-tag
<220> FEATURE:
<221> NAME/KEY: misc_feature
<222> LOCATION: (934)..(939)
<223> OTHER INFORMATION: Eco47III restriction site

<400> SEQUENCE: 9 cat atg gca cgt aaa att ggt att att ggt ctg ggt aat gtt ggt gca        48
    Met Ala Arg Lys Ile Gly Ile Ile Gly Leu Gly Asn Val Gly Ala
    1               5                   10                  15 gca gtt gca cat ggt ctg att gca cag ggt gtt gca gat gat tat gtt        96
Ala Val Ala His Gly Leu Ile Ala Gln Gly Val Ala Asp Asp Tyr Val
                20                  25                  30 ttt att gat gcc aac gaa gcc aaa gtg aaa gcc gat cag att gat ttt       144
Phe Ile Asp Ala Asn Glu Ala Lys Val Lys Ala Asp Gln Ile Asp Phe
            35                  40                  45 cag gat gca atg gca aat ctg gaa gcg cat ggt aat att gtg att aat       192
Gln Asp Ala Met Ala Asn Leu Glu Ala His Gly Asn Ile Val Ile Asn
        50                  55                  60 gat tgg gca gca ctg gca gat gca gat gtt gtt att agc acc ctg ggt       240
Asp Trp Ala Ala Leu Ala Asp Ala Asp Val Val Ile Ser Thr Leu Gly
65                  70                  75 aac att aaa ctg cag cag gat aat ccg acc ggt gat cgt ttt gca gaa       288
Asn Ile Lys Leu Gln Gln Asp Asn Pro Thr Gly Asp Arg Phe Ala Glu
80                  85                  90                  95 ctg aaa ttt acc agc agc atg gtt cag agc gtt ggc acc aat ctg aaa       336
Leu Lys Phe Thr Ser Ser Met Val Gln Ser Val Gly Thr Asn Leu Lys
                100                 105                 110 gaa agc ggt ttt cat ggt gtt ctg gtt gtg att agc aat ccg gtt gat       384
Glu Ser Gly Phe His Gly Val Leu Val Val Ile Ser Asn Pro Val Asp
            115                 120                 125 gtt att acc gca ctg ttt cag cat gtt acc ggt ttt ccg gca cat aaa       432
Val Ile Thr Ala Leu Phe Gln His Val Thr Gly Phe Pro Ala His Lys
        130                 135                 140
```

-continued

```
gtt att ggc acc ggc acc ctg ctg gat acc gca cgt atg cag cgt gca      480
Val Ile Gly Thr Gly Thr Leu Leu Asp Thr Ala Arg Met Gln Arg Ala
    145                 150                 155 gtt ggt gaa gca ttt gat ctg gac cct cgt agc gtt agc ggt tat aat      528
Val Gly Glu Ala Phe Asp Leu Asp Pro Arg Ser Val Ser Gly Tyr Asn
160                 165                 170                 175 ctg ggt gaa cat ggt aat tca cag ttt gtt gca tgg tca acc gtt cgt      576
Leu Gly Glu His Gly Asn Ser Gln Phe Val Ala Trp Ser Thr Val Arg
                    180                 185                 190 gtt atg ggt cag ccg att gtt acc ctg gcc gat gcc ggt gat att gat      624
Val Met Gly Gln Pro Ile Val Thr Leu Ala Asp Ala Gly Asp Ile Asp
                195                 200                 205 ctg gca gca att gaa gaa gaa gca cgt aaa ggc ggt ttt acc gtt ctg      672
Leu Ala Ala Ile Glu Glu Glu Ala Arg Lys Gly Gly Phe Thr Val Leu
            210                 215                 220 aat ggt aaa ggt tat acc agc tat ggt gtt gca acc agc gca att cgt      720
Asn Gly Lys Gly Tyr Thr Ser Tyr Gly Val Ala Thr Ser Ala Ile Arg
        225                 230                 235 att gca aaa gca gtt atg gcg gat gca cat gcc gaa ctg gtt gtt agc      768
Ile Ala Lys Ala Val Met Ala Asp Ala His Ala Glu Leu Val Val Ser
240                 245                 250                 255 aat cgt cgt gat gat atg ggt atg tat ctg agc tat ccg gca att att      816
Asn Arg Arg Asp Asp Met Gly Met Tyr Leu Ser Tyr Pro Ala Ile Ile
                    260                 265                 270 ggc cgt gat ggt gtg ctg gca gaa acc acc ctg gat ctg acc acc gat      864
Gly Arg Asp Gly Val Leu Ala Glu Thr Thr Leu Asp Leu Thr Thr Asp
                275                 280                 285 gaa caa gaa aaa ctg ctg cag agc cgt gat tat att cag cag cgt ttt      912
Glu Gln Glu Lys Leu Leu Gln Ser Arg Asp Tyr Ile Gln Gln Arg Phe
            290                 295                 300 gat gaa att gtg gac acc ctg agc gct cac cat cac cat cac cat taa      960
Asp Glu Ile Val Asp Thr Leu Ser Ala His His His His His His
        305                 310                 315
```

<210> SEQ ID NO 10
<211> LENGTH: 318
<212> TYPE: PRT
<213> ORGANISM: Lactobacillus confuses

<400> SEQUENCE: 10

```
Met Ala Arg Lys Ile Gly Ile Gly Leu Gly Asn Val Gly Ala Ala
1               5                   10                  15

Val Ala His Gly Leu Ile Ala Gln Gly Val Ala Asp Asp Tyr Val Phe
                20                  25                  30

Ile Asp Ala Asn Glu Ala Lys Val Lys Ala Asp Gln Ile Asp Phe Gln
            35                  40                  45

Asp Ala Met Ala Asn Leu Glu Ala His Gly Asn Ile Val Ile Asn Asp
        50                  55                  60

Trp Ala Ala Leu Ala Asp Ala Asp Val Val Ile Ser Thr Leu Gly Asn
65                  70                  75                  80

Ile Lys Leu Gln Gln Asp Asn Pro Thr Gly Asp Arg Phe Ala Glu Leu
                85                  90                  95

Lys Phe Thr Ser Ser Met Val Gln Ser Val Gly Thr Asn Leu Lys Glu
            100                 105                 110

Ser Gly Phe His Gly Val Leu Val Ile Ser Asn Pro Val Asp Val
        115                 120                 125

Ile Thr Ala Leu Phe Gln His Val Thr Gly Phe Pro Ala His Lys Val
    130                 135                 140
```

```
Ile Gly Thr Gly Thr Leu Leu Asp Thr Ala Arg Met Gln Arg Ala Val
145                 150                 155                 160

Gly Glu Ala Phe Asp Leu Asp Pro Arg Ser Val Gly Tyr Asn Leu
            165                 170                 175

Gly Glu His Gly Asn Ser Gln Phe Val Ala Trp Ser Thr Val Arg Val
        180                 185                 190

Met Gly Gln Pro Ile Val Thr Leu Ala Asp Ala Gly Asp Ile Asp Leu
        195                 200                 205

Ala Ala Ile Glu Glu Glu Ala Arg Lys Gly Gly Phe Thr Val Leu Asn
210                 215                 220

Gly Lys Gly Tyr Thr Ser Tyr Gly Val Ala Thr Ser Ala Ile Arg Ile
225                 230                 235                 240

Ala Lys Ala Val Met Ala Asp Ala His Ala Glu Leu Val Val Ser Asn
                245                 250                 255

Arg Arg Asp Asp Met Gly Met Tyr Leu Ser Tyr Pro Ala Ile Ile Gly
                260                 265                 270

Arg Asp Gly Val Leu Ala Glu Thr Thr Leu Asp Leu Thr Thr Asp Glu
            275                 280                 285

Gln Glu Lys Leu Leu Gln Ser Arg Asp Tyr Ile Gln Gln Arg Phe Asp
        290                 295                 300

Glu Ile Val Asp Thr Leu Ser Ala His His His His His His
305                 310                 315
```

<210> SEQ ID NO 11
<211> LENGTH: 1252
<212> TYPE: DNA
<213> ORGANISM: Pseudomonas sp. 101
<220> FEATURE:
<221> NAME/KEY: CDS
<222> LOCATION: (1)..(1248)
<223> OTHER INFORMATION: sequence of PseFDH from Pseudomonas sp. 101
      optimized for the codon usage of Escherichia coli with an
      amino-terminal His6-tag
<220> FEATURE:
<221> NAME/KEY: misc_feature
<222> LOCATION: (37)..(41)
<223> OTHER INFORMATION: KasI restriction site
<220> FEATURE:
<221> NAME/KEY: misc_feature
<222> LOCATION: (1247)..(1252)
<223> OTHER INFORMATION: HindIII restriction site

<400> SEQUENCE: 11

```
atg gct agc aga gga tcg cat cac cat cac cat cac ggc gcc atg gca      48
Met Ala Ser Arg Gly Ser His His His His His His Gly Ala Met Ala
1               5                   10                  15 aaa gtt ctg tgt gtt ctg tat gat gat ccg gtt gat ggt tat ccg aaa      96
Lys Val Leu Cys Val Leu Tyr Asp Asp Pro Val Asp Gly Tyr Pro Lys
            20                  25                  30 acc tat gca cgt gat gat ctg ccg aaa att gat cat tat ccg ggt ggt     144
Thr Tyr Ala Arg Asp Asp Leu Pro Lys Ile Asp His Tyr Pro Gly Gly
        35                  40                  45 cag acc ctg ccg acc ccg aaa gca att gat ttt aca ccg ggt cag ctg     192
Gln Thr Leu Pro Thr Pro Lys Ala Ile Asp Phe Thr Pro Gly Gln Leu
    50                  55                  60 ctg ggt agc gtt agc ggt gaa ctg ggt ctg cgt aaa tat ctg gaa agc     240
Leu Gly Ser Val Ser Gly Glu Leu Gly Leu Arg Lys Tyr Leu Glu Ser
65                  70                  75                  80 aat ggt cat acc ctg gtt gtt acc agc gat aaa gat ggt ccg gat agc     288
Asn Gly His Thr Leu Val Val Thr Ser Asp Lys Asp Gly Pro Asp Ser
            85                  90                  95
```

```
gtt ttt gaa cgt gaa ctg gtt gat gcc gat gtt gtt att agc cag ccg    336
Val Phe Glu Arg Glu Leu Val Asp Ala Asp Val Val Ile Ser Gln Pro
        100                 105                 110 ttt tgg cct gca tat ctg aca ccg gaa cgt att gca aaa gcc aaa aat    384
Phe Trp Pro Ala Tyr Leu Thr Pro Glu Arg Ile Ala Lys Ala Lys Asn
        115                 120                 125 ctg aaa ctg gca ctg acc gca ggt att ggt agc gat cat gtt gat ctg    432
Leu Lys Leu Ala Leu Thr Ala Gly Ile Gly Ser Asp His Val Asp Leu
130                 135                 140 cag agc gca att gat cgt aat gtt acc gtt gca gaa gtg acc tat tgt    480
Gln Ser Ala Ile Asp Arg Asn Val Thr Val Ala Glu Val Thr Tyr Cys
145                 150                 155                 160 aat agc att agc gtt gcc gaa cat gtg gtt atg atg att ctg agc ctg    528
Asn Ser Ile Ser Val Ala Glu His Val Val Met Met Ile Leu Ser Leu
                165                 170                 175 gtt cgt aat tat ctg ccg agc cat gaa tgg gca cgt aaa ggt ggt tgg    576
Val Arg Asn Tyr Leu Pro Ser His Glu Trp Ala Arg Lys Gly Gly Trp
            180                 185                 190 aat att gca gat tgt gtt agc cat gcc tat gat ctg gaa gcc atg cat    624
Asn Ile Ala Asp Cys Val Ser His Ala Tyr Asp Leu Glu Ala Met His
        195                 200                 205 gtt ggc acc gtt gcc gca ggt cgt att ggt ctg gca gtt ctg cgt cgt    672
Val Gly Thr Val Ala Ala Gly Arg Ile Gly Leu Ala Val Leu Arg Arg
210                 215                 220 ctg gct ccg ttt gat gtt cat ctg cat tat acc gat cgt cat cgt ctg    720
Leu Ala Pro Phe Asp Val His Leu His Tyr Thr Asp Arg His Arg Leu
225                 230                 235                 240 ccg gaa agc gtt gaa aaa gaa ctg aat ctg acc tgg cat gca acc cgt    768
Pro Glu Ser Val Glu Lys Glu Leu Asn Leu Thr Trp His Ala Thr Arg
                245                 250                 255 gaa gat atg tat ccg gtt tgt gat gtt gtg acc ctg aat tgt ccg ctg    816
Glu Asp Met Tyr Pro Val Cys Asp Val Val Thr Leu Asn Cys Pro Leu
            260                 265                 270 cat ccg gaa acc gaa cac atg att aat gat gaa acc ctg aaa ctg ttt    864
His Pro Glu Thr Glu His Met Ile Asn Asp Glu Thr Leu Lys Leu Phe
        275                 280                 285 aaa cgc ggt gcc tat att gtt aat acc gca cgt ggt aaa ctg tgt gat    912
Lys Arg Gly Ala Tyr Ile Val Asn Thr Ala Arg Gly Lys Leu Cys Asp
290                 295                 300 cgt gat gca gtt gca cgt gcc ctg gaa agc ggt cgc ctg gca ggt tat    960
Arg Asp Ala Val Ala Arg Ala Leu Glu Ser Gly Arg Leu Ala Gly Tyr
305                 310                 315                 320 gcc ggt gat gtt tgg ttt ccg cag cct gca ccg aaa gat cat ccg tgg   1008
Ala Gly Asp Val Trp Phe Pro Gln Pro Ala Pro Lys Asp His Pro Trp
                325                 330                 335 cgt acc atg ccg tat aat ggt atg aca ccg cat att agc ggc acc acc   1056
Arg Thr Met Pro Tyr Asn Gly Met Thr Pro His Ile Ser Gly Thr Thr
            340                 345                 350 ctg acc gca cag gca cgt tat gca gca ggc acc cgt gaa att ctg gaa   1104
Leu Thr Ala Gln Ala Arg Tyr Ala Ala Gly Thr Arg Glu Ile Leu Glu
        355                 360                 365 tgt ttt ttt gaa ggt cgt ccg att cgt gat gaa tat ctg att gtt cag   1152
Cys Phe Phe Glu Gly Arg Pro Ile Arg Asp Glu Tyr Leu Ile Val Gln
370                 375                 380 ggt ggc gca ctg gca ggt aca ggt gca cat agc tat agc aaa ggt aat   1200
Gly Gly Ala Leu Ala Gly Thr Gly Ala His Ser Tyr Ser Lys Gly Asn
385                 390                 395                 400 gca acc ggt ggt agc gaa gaa gca gca aaa ttc aaa aaa gcc gtg taa   1248
Ala Thr Gly Gly Ser Glu Glu Ala Ala Lys Phe Lys Lys Ala Val
```

```
                       405                 410                 415
gctt                                                                       1252

<210> SEQ ID NO 12
<211> LENGTH: 415
<212> TYPE: PRT
<213> ORGANISM: Pseudomonas sp. 101

<400> SEQUENCE: 12

Met Ala Ser Arg Gly Ser His His His His His Gly Ala Met Ala
1               5                   10                  15

Lys Val Leu Cys Val Leu Tyr Asp Asp Pro Val Asp Gly Tyr Pro Lys
                20                  25                  30

Thr Tyr Ala Arg Asp Asp Leu Pro Lys Ile Asp His Tyr Pro Gly Gly
        35                  40                  45

Gln Thr Leu Pro Thr Pro Lys Ala Ile Asp Phe Thr Pro Gly Gln Leu
    50                  55                  60

Leu Gly Ser Val Ser Gly Glu Leu Gly Leu Arg Lys Tyr Leu Glu Ser
65                  70                  75                  80

Asn Gly His Thr Leu Val Val Thr Ser Asp Lys Asp Gly Pro Asp Ser
                85                  90                  95

Val Phe Glu Arg Glu Leu Val Asp Ala Asp Val Val Ile Ser Gln Pro
            100                 105                 110

Phe Trp Pro Ala Tyr Leu Thr Pro Glu Arg Ile Ala Lys Ala Lys Asn
        115                 120                 125

Leu Lys Leu Ala Leu Thr Ala Gly Ile Gly Ser Asp His Val Asp Leu
130                 135                 140

Gln Ser Ala Ile Asp Arg Asn Val Thr Val Ala Glu Val Thr Tyr Cys
145                 150                 155                 160

Asn Ser Ile Ser Val Ala Glu His Val Val Met Met Ile Leu Ser Leu
                165                 170                 175

Val Arg Asn Tyr Leu Pro Ser His Glu Trp Ala Arg Lys Gly Gly Trp
            180                 185                 190

Asn Ile Ala Asp Cys Val Ser His Ala Tyr Asp Leu Glu Ala Met His
        195                 200                 205

Val Gly Thr Val Ala Ala Gly Arg Ile Gly Leu Ala Val Leu Arg Arg
    210                 215                 220

Leu Ala Pro Phe Asp Val His Leu His Tyr Thr Asp Arg His Arg Leu
225                 230                 235                 240

Pro Glu Ser Val Glu Lys Glu Leu Asn Leu Thr Trp His Ala Thr Arg
                245                 250                 255

Glu Asp Met Tyr Pro Val Cys Asp Val Val Thr Leu Asn Cys Pro Leu
            260                 265                 270

His Pro Glu Thr Glu His Met Ile Asn Asp Glu Thr Leu Lys Leu Phe
        275                 280                 285

Lys Arg Gly Ala Tyr Ile Val Asn Thr Ala Arg Gly Lys Leu Cys Asp
    290                 295                 300

Arg Asp Ala Val Ala Arg Ala Leu Glu Ser Gly Arg Leu Ala Gly Tyr
305                 310                 315                 320

Ala Gly Asp Val Trp Phe Pro Gln Pro Ala Pro Lys Asp His Pro Trp
                325                 330                 335

Arg Thr Met Pro Tyr Asn Gly Met Thr Pro His Ile Ser Gly Thr Thr
            340                 345                 350

Leu Thr Ala Gln Ala Arg Tyr Ala Ala Gly Thr Arg Glu Ile Leu Glu
```

```
                    355                 360                 365
Cys Phe Phe Glu Gly Arg Pro Ile Arg Asp Glu Tyr Leu Ile Val Gln
    370                 375                 380

Gly Gly Ala Leu Ala Gly Thr Gly Ala His Ser Tyr Ser Lys Gly Asn
385                 390                 395                 400

Ala Thr Gly Gly Ser Glu Glu Ala Ala Lys Phe Lys Lys Ala Val
                405                 410                 415
```

<210> SEQ ID NO 13
<211> LENGTH: 1141
<212> TYPE: DNA
<213> ORGANISM: Candida boidinii
<220> FEATURE:
<221> NAME/KEY: CDS
<222> LOCATION: (1)..(1137)
<223> OTHER INFORMATION: sequence of CboFDH(C23A/F285S) from Candida
      boidinii optimized for the codon usage of Escherichia coli with an
      amino-terminal His6-tag
<220> FEATURE:
<221> NAME/KEY: misc_feature
<222> LOCATION: (37)..(42)
<223> OTHER INFORMATION: KasI restriction site
<220> FEATURE:
<221> NAME/KEY: misc_feature
<222> LOCATION: (1136)..(1141)
<223> OTHER INFORMATION: HindIII restriction site

<400> SEQUENCE: 13

```
atg gct agc aga gga tcg cat cac cat cac cat cac ggc gcc atg aaa      48
Met Ala Ser Arg Gly Ser His His His His His His Gly Ala Met Lys
1               5                   10                  15 att gtt ctg gtt ctg tat gat gca ggt aaa cat gca gca gat gaa gaa      96
Ile Val Leu Val Leu Tyr Asp Ala Gly Lys His Ala Ala Asp Glu Glu
                20                  25                  30 aaa ctg tat ggt gcc acc gaa aat aaa ctg ggt att gca aat tgg ctg     144
Lys Leu Tyr Gly Ala Thr Glu Asn Lys Leu Gly Ile Ala Asn Trp Leu
            35                  40                  45 aaa gat cag ggt cat gaa ctg att acc acc agt gat aaa gaa ggt gaa     192
Lys Asp Gln Gly His Glu Leu Ile Thr Thr Ser Asp Lys Glu Gly Glu
        50                  55                  60 acc agc gaa ctg gat aaa cat att ccg gat gcc gat att atc att acc     240
Thr Ser Glu Leu Asp Lys His Ile Pro Asp Ala Asp Ile Ile Ile Thr
65                  70                  75                  80 acc ccg ttt cat ccg gca tat atc acc aaa gaa cgt ctg gat aaa gcc     288
Thr Pro Phe His Pro Ala Tyr Ile Thr Lys Glu Arg Leu Asp Lys Ala
                85                  90                  95 aaa aat ctg aaa ctg gtt gtt gtt gcc ggt gtt ggt agc gat cat att     336
Lys Asn Leu Lys Leu Val Val Val Ala Gly Val Gly Ser Asp His Ile
            100                 105                 110 gat ctg gat tat atc aat cag acc ggc aaa aaa atc agc gtt ctg gaa     384
Asp Leu Asp Tyr Ile Asn Gln Thr Gly Lys Lys Ile Ser Val Leu Glu
        115                 120                 125 gtt acc ggt agc aat gtt gtt agc gtt gca gaa cat gtt gtt atg acc     432
Val Thr Gly Ser Asn Val Val Ser Val Ala Glu His Val Val Met Thr
    130                 135                 140 atg ctg gtt ctg gtg cgc aat ttt gtt ccg gca cat gag cag att att     480
Met Leu Val Leu Val Arg Asn Phe Val Pro Ala His Glu Gln Ile Ile
145                 150                 155                 160 aac cat gat tgg gaa gtt gca gcc att gca aaa gat gcc tat gat att     528
Asn His Asp Trp Glu Val Ala Ala Ile Ala Lys Asp Ala Tyr Asp Ile
                165                 170                 175 gaa ggt aaa acc att gca acc att ggt gca ggt cgt att ggt tat cgt     576
Glu Gly Lys Thr Ile Ala Thr Ile Gly Ala Gly Arg Ile Gly Tyr Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 180 |     |     |     |     | 185 |     |     |     |     | 190 |     |     |      |
| gtt | ctg | gaa | cgt | ctg | ctg | ccg | ttt | aat | ccg | aaa | gaa | ctg | ctg | tat | tat | 624  |
| Val | Leu | Glu | Arg | Leu | Leu | Pro | Phe | Asn | Pro | Lys | Glu | Leu | Leu | Tyr | Tyr |      |
|     |     |     | 195 |     |     |     |     | 200 |     |     |     |     | 205 |     |     |      |
| gat | tat | cag | gca | ctg | ccg | aaa | gaa | gcc | gaa | gaa | aaa | gtt | ggt | gcc | cgt | 672  |
| Asp | Tyr | Gln | Ala | Leu | Pro | Lys | Glu | Ala | Glu | Glu | Lys | Val | Gly | Ala | Arg |      |
|     |     | 210 |     |     |     |     | 215 |     |     |     |     | 220 |     |     |     |      |
| cgt | gtt | gaa | aat | att | gaa | gaa | ctg | gtt | gca | cag | gcc | gat | att | gtt | acc | 720  |
| Arg | Val | Glu | Asn | Ile | Glu | Glu | Leu | Val | Ala | Gln | Ala | Asp | Ile | Val | Thr |      |
| 225 |     |     |     |     | 230 |     |     |     |     | 235 |     |     |     |     | 240 |      |
| gtt | aat | gca | ccg | ctg | cat | gcc | ggt | aca | aaa | ggt | ctg | att | aac | aaa | gag | 768  |
| Val | Asn | Ala | Pro | Leu | His | Ala | Gly | Thr | Lys | Gly | Leu | Ile | Asn | Lys | Glu |      |
|     |     |     |     | 245 |     |     |     |     | 250 |     |     |     |     | 255 |     |      |
| ctg | ctg | agc | aaa | ttc | aaa | aaa | ggt | gca | tgg | ctg | gtt | aat | acc | gca | cgt | 816  |
| Leu | Leu | Ser | Lys | Phe | Lys | Lys | Gly | Ala | Trp | Leu | Val | Asn | Thr | Ala | Arg |      |
|     |     |     | 260 |     |     |     |     | 265 |     |     |     |     | 270 |     |     |      |
| ggt | gca | att | tgt | gtt | gcc | gaa | gat | gtt | gca | gca | gca | ctg | gaa | agc | ggt | 864  |
| Gly | Ala | Ile | Cys | Val | Ala | Glu | Asp | Val | Ala | Ala | Ala | Leu | Glu | Ser | Gly |      |
|     |     |     | 275 |     |     |     |     | 280 |     |     |     |     | 285 |     |     |      |
| cag | ctg | cgt | ggt | tat | ggt | ggt | gat | gtt | tgg | agt | ccg | cag | cct | gca | ccg | 912  |
| Gln | Leu | Arg | Gly | Tyr | Gly | Gly | Asp | Val | Trp | Ser | Pro | Gln | Pro | Ala | Pro |      |
|     |     | 290 |     |     |     |     | 295 |     |     |     |     | 300 |     |     |     |      |
| aaa | gat | cat | ccg | tgg | cgt | gat | atg | cgt | aac | aaa | tat | ggt | gcc | ggt | aat | 960  |
| Lys | Asp | His | Pro | Trp | Arg | Asp | Met | Arg | Asn | Lys | Tyr | Gly | Ala | Gly | Asn |      |
| 305 |     |     |     |     | 310 |     |     |     |     | 315 |     |     |     |     | 320 |      |
| gca | atg | aca | ccg | cat | tat | agc | ggc | acc | acc | ctg | gat | gca | cag | acc | cgt | 1008 |
| Ala | Met | Thr | Pro | His | Tyr | Ser | Gly | Thr | Thr | Leu | Asp | Ala | Gln | Thr | Arg |      |
|     |     |     |     | 325 |     |     |     |     | 330 |     |     |     |     | 335 |     |      |
| tat | gca | gaa | ggc | acc | aaa | aac | att | ctg | gaa | agt | ttt | ttc | acc | ggc | aaa | 1056 |
| Tyr | Ala | Glu | Gly | Thr | Lys | Asn | Ile | Leu | Glu | Ser | Phe | Phe | Thr | Gly | Lys |      |
|     |     |     | 340 |     |     |     |     | 345 |     |     |     |     | 350 |     |     |      |
| ttc | gat | tat | cgt | ccg | cag | gat | att | att | ctg | ctg | aat | ggt | gaa | tat | gtg | 1104 |
| Phe | Asp | Tyr | Arg | Pro | Gln | Asp | Ile | Ile | Leu | Leu | Asn | Gly | Glu | Tyr | Val |      |
|     |     |     | 355 |     |     |     |     | 360 |     |     |     |     | 365 |     |     |      |
| acc | aaa | gcc | tat | ggc | aaa | cac | gac | aaa | aaa | taa | gctt |   |     |     |     | 1141 |
| Thr | Lys | Ala | Tyr | Gly | Lys | His | Asp | Lys | Lys |     |     |     |     |     |     |      |
|     | 370 |     |     |     |     | 375 |     |     |     |     |     |     |     |     |     |      |

<210> SEQ ID NO 14
<211> LENGTH: 378
<212> TYPE: PRT
<213> ORGANISM: Candida boidinii

<400> SEQUENCE: 14

Met Ala Ser Arg Gly Ser His His His His His His Gly Ala Met Lys
1               5                   10                  15

Ile Val Leu Val Leu Tyr Asp Ala Gly Lys His Ala Ala Asp Glu Glu
                20                  25                  30

Lys Leu Tyr Gly Ala Thr Glu Asn Lys Leu Gly Ile Ala Asn Trp Leu
            35                  40                  45

Lys Asp Gln Gly His Glu Leu Ile Thr Thr Ser Asp Lys Glu Gly Glu
        50                  55                  60

Thr Ser Glu Leu Asp Lys His Ile Pro Asp Ala Asp Ile Ile Ile Thr
65                  70                  75                  80

Thr Pro Phe His Pro Ala Tyr Ile Thr Lys Glu Arg Leu Asp Lys Ala
                85                  90                  95

Lys Asn Leu Lys Leu Val Val Val Ala Gly Val Gly Ser Asp His Ile
                100                 105                 110

-continued

```
Asp Leu Asp Tyr Ile Asn Gln Thr Gly Lys Lys Ile Ser Val Leu Glu
        115                 120                 125
Val Thr Gly Ser Asn Val Val Ser Val Ala Glu His Val Val Met Thr
        130                 135                 140
Met Leu Val Leu Val Arg Asn Phe Val Pro Ala His Glu Gln Ile Ile
145                 150                 155                 160
Asn His Asp Trp Glu Val Ala Ala Ile Ala Lys Asp Ala Tyr Asp Ile
                165                 170                 175
Glu Gly Lys Thr Ile Ala Thr Ile Gly Ala Gly Arg Ile Gly Tyr Arg
            180                 185                 190
Val Leu Glu Arg Leu Leu Pro Phe Asn Pro Lys Glu Leu Leu Tyr Tyr
        195                 200                 205
Asp Tyr Gln Ala Leu Pro Lys Glu Ala Glu Glu Lys Val Gly Ala Arg
        210                 215                 220
Arg Val Glu Asn Ile Glu Glu Leu Val Ala Gln Ala Asp Ile Val Thr
225                 230                 235                 240
Val Asn Ala Pro Leu His Ala Gly Thr Lys Gly Leu Ile Asn Lys Glu
                245                 250                 255
Leu Leu Ser Lys Phe Lys Lys Gly Ala Trp Leu Val Asn Thr Ala Arg
            260                 265                 270
Gly Ala Ile Cys Val Ala Glu Asp Val Ala Ala Ala Leu Glu Ser Gly
            275                 280                 285
Gln Leu Arg Gly Tyr Gly Gly Asp Val Trp Ser Pro Gln Pro Ala Pro
        290                 295                 300
Lys Asp His Pro Trp Arg Asp Met Arg Asn Lys Tyr Gly Ala Gly Asn
305                 310                 315                 320
Ala Met Thr Pro His Tyr Ser Gly Thr Thr Leu Asp Ala Gln Thr Arg
                325                 330                 335
Tyr Ala Glu Gly Thr Lys Asn Ile Leu Glu Ser Phe Phe Thr Gly Lys
            340                 345                 350
Phe Asp Tyr Arg Pro Gln Asp Ile Ile Leu Leu Asn Gly Glu Tyr Val
        355                 360                 365
Thr Lys Ala Tyr Gly Lys His Asp Lys Lys
370                 375
```

ENZYMATIC METHOD FOR PRODUCING 2-HYDROXY-4-METHYLMERCAPTOBUTANOIC ACID (MHA)

CROSS REFERENCE TO RELATED APPLICATIONS

The present application claims priority under 35 USC § 119 to European application, EP 17166447.7, filed on Apr. 13, 2017, the contents of which is incorporated herein by reference in its entirety.

FIELD OF THE INVENTION

The invention relates to an enzymatic method for producing 2-hydroxy-4-methylmercaptobutanoic acid from 3-methylthio-propanal (3-methylmercaptopropanal (MMP) or "methional").

BACKGROUND OF THE INVENTION

2-Hydroxy-4-methylmercaptobutanoic acid is used as a feed additive in a similar way to methionine and, owing to the structural similarity, is therefore known as methionine hydroxy analog (MHA). Up to the present, MHA has conventionally been obtained from methional, which, in turn, is obtainable by addition of methyl mercaptan (methanethiol) to acrolein, followed by reaction with hydrogen cyanide and subsequent hydrolysis of the 4-methylmercapto-2-hydroxybutanenitrile formed. The need to use hydrogen cyanide is a disadvantage of this process. Owing to the high toxicity of hydrogen cyanide, outlay on safety must be high for the reaction. Another great disadvantage is the ammonium salt formed by the introduction of nitrogen and its subsequent hydrolytic cleavage, which is formed stoichiometrically and causes correspondingly high pollution of waste water. There is therefore a need for an HCN-free process for the production of MHA.

Burrington et al. (U.S. Pat. No. 4,782,173) propose a three-step catalytic conversion of methional to MHA using carbon monoxide as C1 building block. Lehmann et al. (WO 02/16671 A1) disclose a process for the production of MHA by electrochemical carboxylation of methional in an undivided electrolytic cell containing a sacrificial anode, an aprotic solvent and a supporting electrolyte using carbon dioxide as C1 building block.

A fermentative method for producing MHA by culturing microorganisms under nitrogen limitation is proposed by Figge et al. (WO 2012/090022 A1). However, in this case the microorganisms produce methionine, which under nitrogen limitation is used as a nitrogen source to yield its deamination product 4-methylthio-2-oxobutanoic acid (MTOB) and MHA by reduction of MTOB (Ince and Knowles (1986) Arch. Microbiol. 146, 151-158).

Miyazaki et al. (Chem. Commun. (2001) 1800-1801) propose the reverse reaction of pyruvate decarboxylase using carbon dioxide as C1 building block for the synthesis of pyruvic acid (2-oxopropanoic acid) from ethanal (acetaldehyde). The reaction requires a large excess of bicarbonate as carbon dioxide source in order to drive the equilibrium into the opposite direction of decarboxylation. A multienzyme catalytic system including a cofactor regeneration cycle that uses a carbonate-bicarbonate buffer and ethanol to produce L-lactate via acetaldehyde and pyruvic acid was proposed by Tong et al. (Biotechnol. Bioeng. (2011) 108, 465-469).

Schütte et al. (Appl Microbiol Biotechnol (1984) 19, 167-176) disclose the L-2-hydroxy-isocaproate dehydrogenase from *Lactobacillus confusus* catalyzing the NADH-dependent reduction of α-keto acids to α-hydroxy acids.

Wichmann et al. (Biotechnol. Bioeng. (1981) 23, 2789-2802) proposed an NADH-dependent enzyme, L-leucine dehydrogenase (LeuDH), for the reductive amination of 2-oxo-4-methylpentanoic acid (α-ketoisocaproate) to L-leucine together with a biocatalytic NADH regeneration system using formate and formate dehydrogenase.

DESCRIPTION OF THE INVENTION

The object of the present invention is to provide a novel process for the production of MHA, in which, on the one hand, methional is used as a starting component and, on the other hand, instead of HCN carbon dioxide is used as C1 building block yielding D- or L-MHA.

The object is achieved by a method for producing D- or L-2-hydroxy-4-methylmercaptobutanoic acid (MHA), comprising a step of reacting a mixture comprising 3-(methylthio)-propanal (methional), carbon dioxide, a decarboxylase, its corresponding cofactor, an alcohol dehydrogenase and NADH or NADPH to form D- or L-2-hydroxy-4-methylmercaptobutanoic acid (MHA) or a salt thereof.

Without willing to be bound by theory, it is thought that initially the decarboxylase in the mixture catalyzes its reverse reaction, i.e. the carboxylation of methional with carbon dioxide ($CO_2$), which leads to the intermediate product 4-methylthio-2-oxobutanoic acid (MTOB), i.e. an α-keto acid (2-oxo acid). Second, the α-carbonyl group of MTOB is reduced to the hydroxyl group in a stereospecific and NADH- (or, alternatively, NADPH-) dependent reaction catalyzed by an alcohol dehydrogenase to yield MHA. FIG. 1 shows a scheme for this two-step biocatalytic synthesis of MHA from methional. The corresponding cofactor of the decarboxylase preferably comprises thiamine pyrophosphate (ThDP).

Decarboxylases that are suitable for the carboxylation of methional are for example pyruvate decarboxylase Pdc1, which originates from *Saccharomyces cerevisiae*, phenylpyruvate decarboxylase Aro10, which originates from *Saccharomyces cerevisiae*, and branched chain decarboxylase KdcA, which originates from *Lactococcus lactis*, as well as mutants and variants of these decarboxylase having decarboxylase activity.

The method according to the present invention is suitable for producing D-2-hydroxy-4-methylmercapto-butanoic acid (D-MHA) as well as L-2-hydroxy-4-methylmercapto-butanoic acid (L-MHA). In case of the production of D-MHA a suitable alcohol dehydrogenase is for example a D-hydroxyisocaproate dehydrogenase, preferably D-HicDH from *Lactobacillus casei* or its mutants and variants having alcohol dehydrogenase activity, whereas in case that the production of L-MHA is desired, a L-hydroxyisocaproate dehydrogenase, preferably L-HicDH from *Lactobacillus confusus* or its mutants and variants having alcohol dehydrogenase activity may for example be chosen as an alcohol dehydrogenase.

In the method according to the present invention the carbon dioxide is preferably applied to the reaction mixture at a pressure from 10 to 7400 kPa (from 0.1 to 74 bar), preferably from 100 to 1000 kPa (1 to 10 bar), more preferably from 200 to 800 kPa (2 to 8 bar).

Optionally, in the method according to the present invention the mixture may further comprise formic acid or a salt thereof and a formate dehydrogenase. In that case regeneration of the NADH consumed in the method according to the present invention can be achieved under consumption of formate and formation of carbon dioxide (FIG. 1). The carbon dioxide may serve as substrate for the reverse decarboxylation reaction described above.

Suitable formate dehydrogenases are for example formate dehydrogenase from *Pseudomonas* sp., e.g. formate dehydrogenase PseFDH from *Pseudomonas* sp. 101, and formate dehydrogenase from *Candida* sp., e.g. formate dehydrogenase from *Candida boidinii* optionally carrying the amino acid substitutions C23A and F285 S, as well as mutants and variants of these formate dehydrogenases having formate dehydrogenase activity.

Examples for enzymes that are suitable for the method according to the present invention are summarized in Table 1. Enzymes are principally classified and named according to the reaction they catalyse. The chemical reaction catalysed is the specific property that distinguishes one enzyme from another and, therefore, this is used as the basis for the classification and naming of enzymes according to the Enzyme Nomenclature as recommended by the Nomenclature Committee of the International Union of Biochemistry and Molecular Biology [Enzyme Nomenclature. Recommendations 1992, Academic Press, 1992, San Diego, Calif., ISBN 0-12-227164-5 (hardback), 0-12-227165-3 (paperback)]. Therefore, decarboxylases catalyzing the decarboxylation of 2-oxocarboxylic acids classified as EC 4.1.1 and alcohol dehydrogenases catalyzing the NADH-dependent reduction of α-keto acids to α-hydroxy acids classified as EC 1.1.1 are all suitable for use in a method according to the present invention. Furthermore, formate dehydrogenases catalyzing the reaction of formate to carbon dioxide under NADH regeneration classified as EC 1.17.1.9 are all suitable for a particular embodiment of the method according to the present invention.

TABLE 1

Enzymes suitable for the synthesis of MHA from Methional

| Enzyme class and example | Organism | Modification(s) | Quaternary structure | SEQ ID No. | Reaction |
|---|---|---|---|---|---|
| Decarboxylase EC 4.1.1 | | | | | |
| Pyruvate decarboxylase: Pdc1 EC 4.1.1.1 (P06169; Killenberg-Jabs et al. (1997) Biochemistry 36, 1900-1905) | *Saccharomyces cerevisiae* | C-terminal $His_6$-tag | tetramer | 1 | Carboxylation of Methional to MTOB |
| Phenylpyruvate decarboxylase: Aro10 EC 4.1.1.43 (Q06408; Kneen et al. (2011) FEBS J. 278, 1842-1853) | *Saccharomyces cerevisiae* | ΔK635; C-terminal $His_6$-tag | dimer | 3 | |
| Branched chain decarboxylase: KdcA EC. 4.1.1.72 (Q6QBS4; Yep et al. (2006) Bioorg. Chem. 34, 325-336) | *Lactococcus lactis* | C-terminal $His_6$-tag | dimer | 5 | |
| Alcohol dehydrogenase EC 1.1.1 | | | | | |
| D-Hydroxyisocaproate dehydrogenase: D-HicDH EC 1.1.1.345 (P17584; Hummel et al. (1985) Appl. Microbiol. Biotechnol. 21, 7-15) | *Lactobacillus casei* | N-terminal $His_6$-tag | dimer | 7 | Reduction of MTOB to D-MHA |
| L-Hydroxyisocaproate dehydrogenase: L-HicDH EC 1.1.1.337 (P14295; Schütte et al. (1984) Appl. Microbiol. Biotechnol. 19, 167-176) | *Lactobacillus confusus* | C-terminal $His_6$-tag | tetramer | 9 | Reduction of MTOB to L-MHA |
| Formate dehydrogenase EC 1.17.1.9 | | | | | |
| Formate dehydrogenase: PseFDH EC 1.17.1.9 (P33160; Egorov et al. (1979) Eur. J. Biochem. 99, 569-576) | *Pseudomonas* sp. 101 | N-terminal $His_6$-tag | dimer | 11 | NADH-regeneration from $NAD^+$ by the oxidation of formate to $CO_2$ |
| Formate dehydrogenase optionally carrying the amino acid substitutions C23A and F285S: CboFDH(C23A/F285S) EC 1.17.1.9 (O13437 for the wild type enzyme; Schütte et al. (1976) Eur. J. Biochem. 62, 151-160; Slusarczyk et al. (2000) Eur. J. Biochem, 267, 1280-1287; Felber (2001) Doctoral Thesis, Heinrich-Heine University Düsseldorf) | *Candida boidinii* | C23A/F285S; N-terminal $His_6$-tag | dimer | 13 | |

First, under a $CO_2$ atmosphere a decarboxylase (e.g., KdcA, Pdc1, Aro10) is employed to catalyze the reverse reaction, i.e. the carboxylation of methional, which leads to the intermediate product 4-methylthio-2-oxobutanoic acid (MTOB). Second, the α-carbonyl group of MTOB is reduced to the hydroxyl group in a stereospecific and NADH- (or, alternatively, NADPH-) dependent reaction catalyzed by an alcohol dehydrogenase (e.g., D/L-HicDH) to yield D- or L-MHA. Optionally, NADH regeneration can be achieved, for example, by a formate dehydrogenase (such as CboFDH(C23A/F285S)/PseFDH) under consumption of formate and generation of $CO_2$.

Figure 2A:
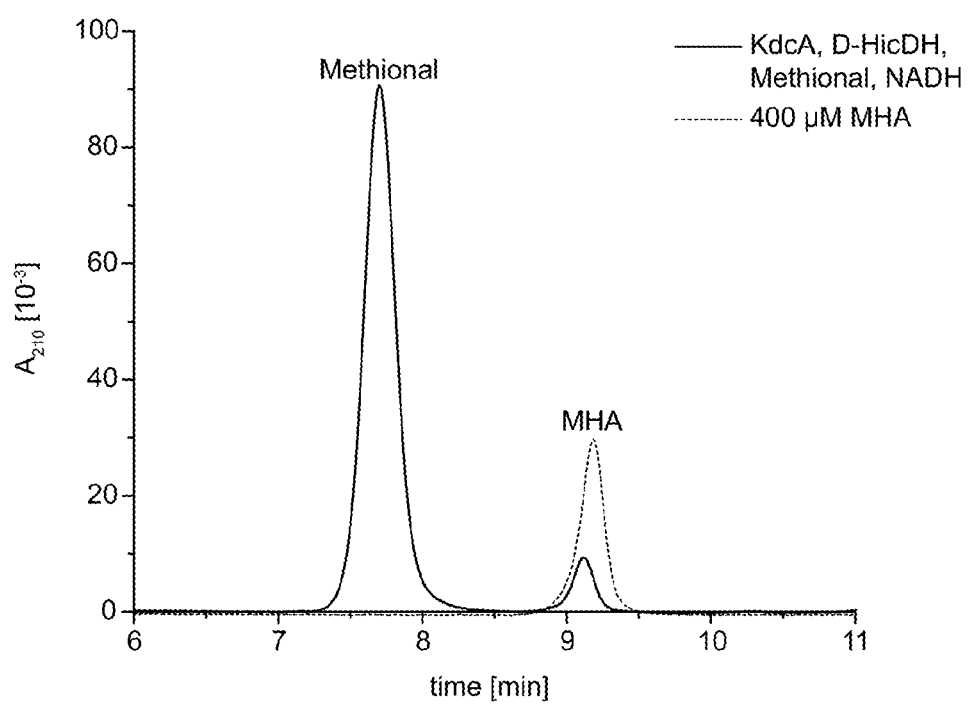

FIG. 2a: Detection of the reaction product D-methionine-hydroxy-analog (D-MHA) using HPLC analytics. The production of D-MHA was verified in a 5 µL sample from Examples 4 and 5 via HPLC analytics using a C18 column (Gemini C18, 4.6×15 mm, 3 µm, 110 Å) and isocratic elution in 4% (v/v) aqueous acetonitrile supplemented with 1% v/v phosphoric acid. Methional and MHA were detected according to their absorption at 210 nm. D-MHA synthesis for 1 h under 2 bar $CO_2$ in the presence of 10 µM KdcA, 1 µM D-HicDH, 4 mM methional, 2 mM NADH. The dotted trace corresponds to an MHA standard with defined concentration.

Figure 2B:
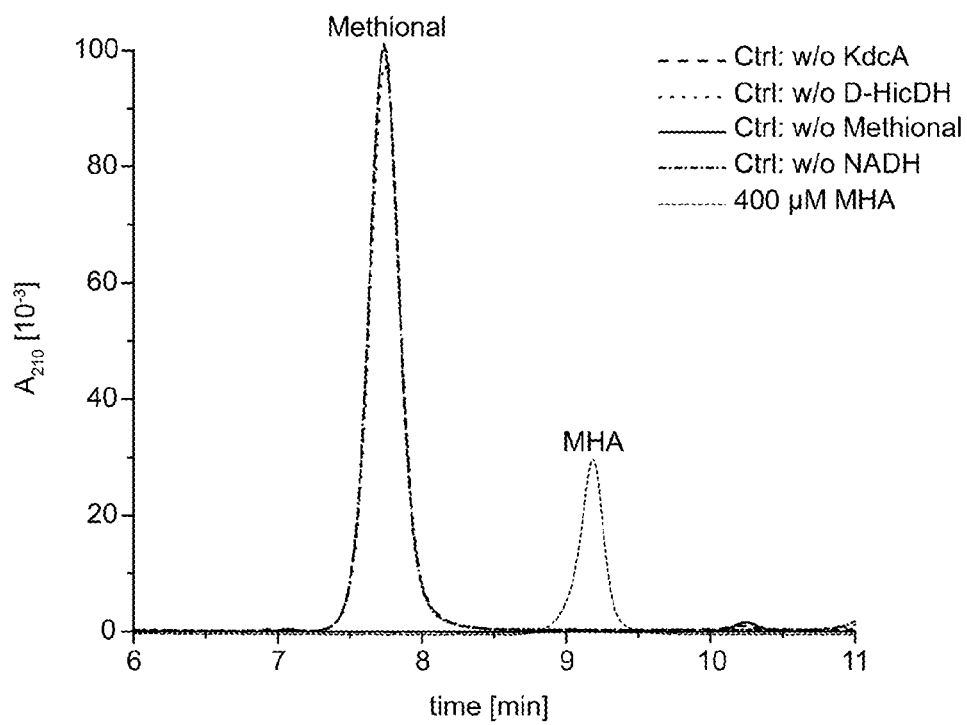

FIG. 2b: Control reactions under the same conditions as in (a) but omitting KdcA, D-HicDH, methional or NADH, respectively.

Figure 2C:
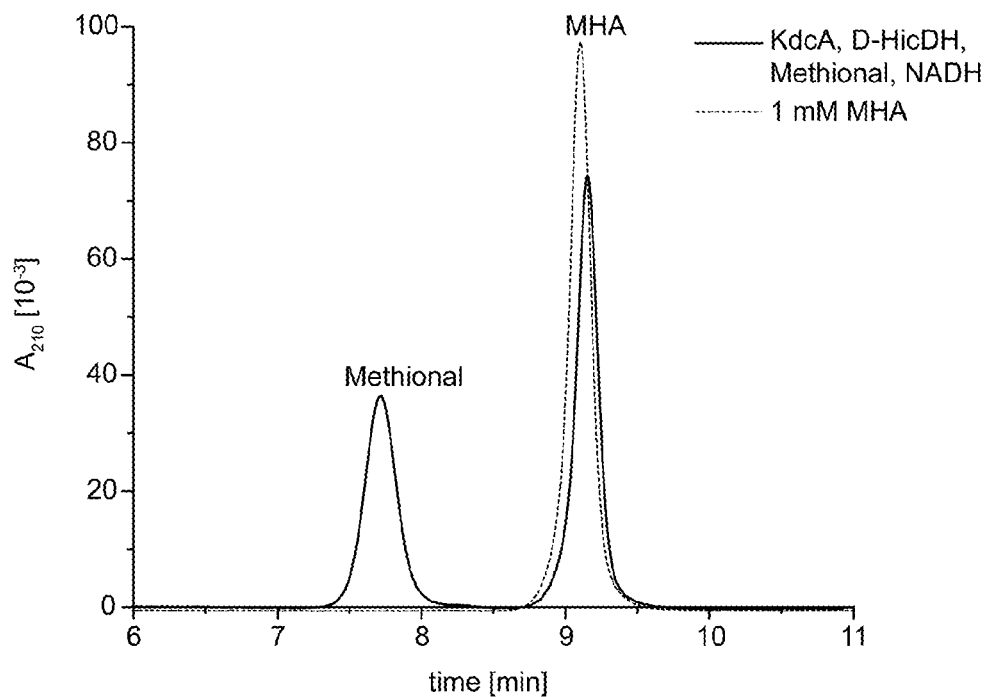

FIG. 2c: Increase of the D-MHA yield, from 3% as shown in (a), to 23%, after optimization of reaction conditions using twice the KdcA concentration, an eightfold reaction time and a fourfold $CO_2$ pressure: 20 µM KdcA, 1 µM D-HicDH, 4 mM methional, 4 mM NADH; catalysis for 8 h under 8 bar $CO_2$.

Figure 2D:
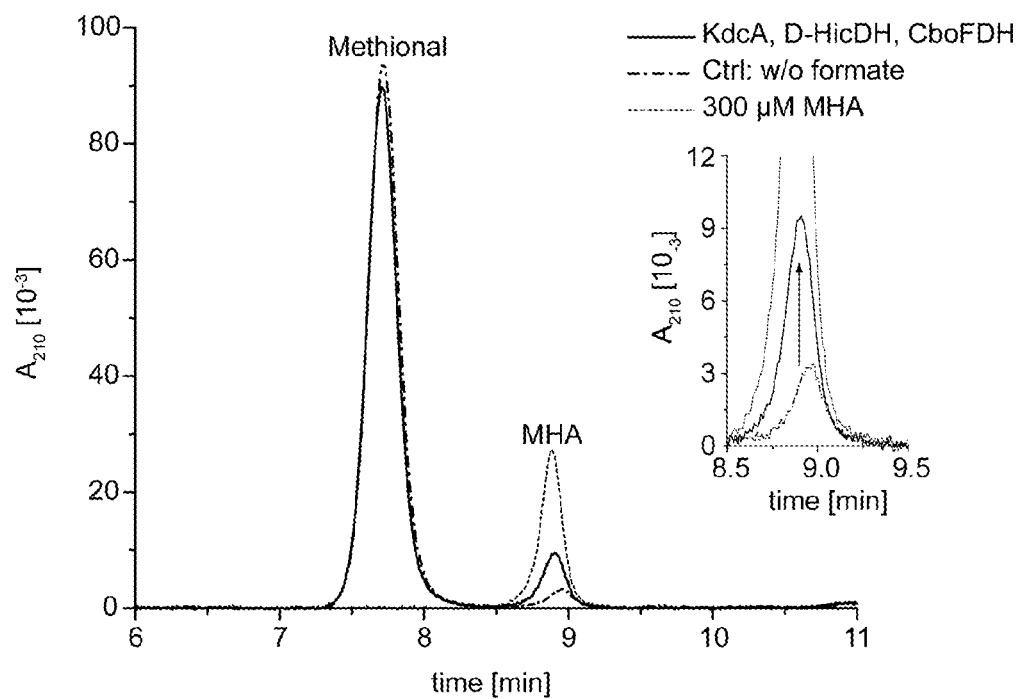

FIG. 2d: Under limiting NADH concentration, the presence of a biocatalytic NADH regeneration system increases the final D-MHA concentration: 10 µM KdcA, 0.5 µM D-HicDH, 10 µM CboFDH(C23A/F285S), 4 mM methional, 80 µM NADH, 25 mM formate; catalysis for 1.5 h under 8 bar $CO_2$. An enlargement of the MHA peak is shown in the inset.

Figure 3A:
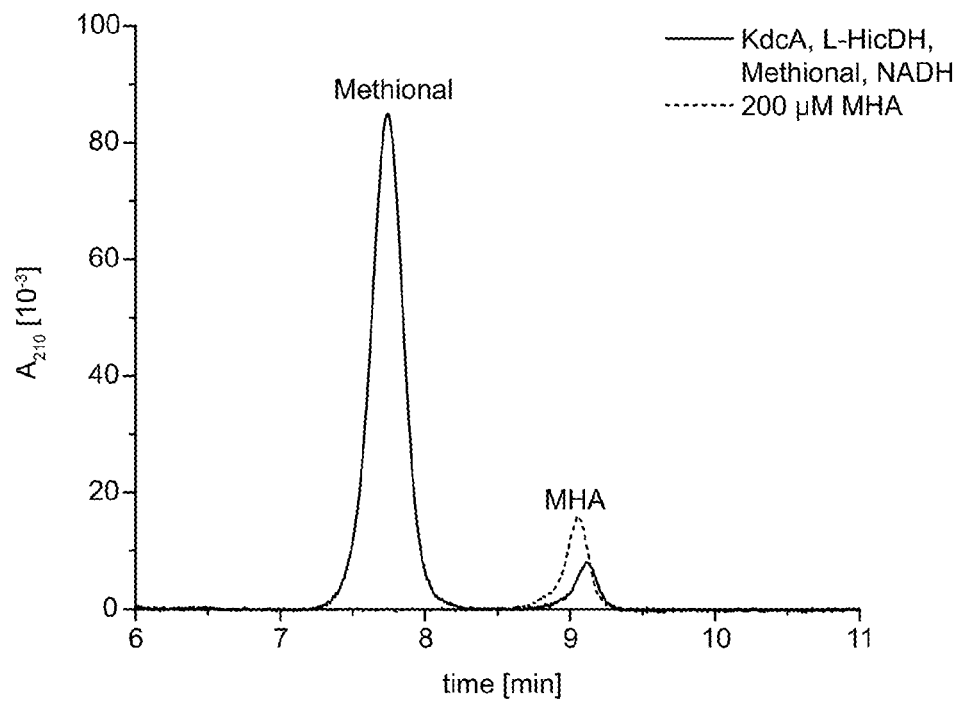

FIG. 3a: Detection of the reaction product L-methionine-hydroxy-analog (L-MHA) using HPLC analytics. The production of L-MHA was verified in a 5 µL sample from Example 6 via HPLC analytics using a C18 column (Gemini C18, 4.6×15 mm, 3 µm, 110 Å) and isocratic elution in 4% (v/v) aqueous acetonitrile supplemented with 1% v/v phosphoric acid. Methional and MHA were detected according to their absorption at 210 nm. L-MHA synthesis for 45 min under 8 bar $CO_2$ in the presence of 20 µM KdcA, 0.5 µM L-HicDH, 4 mM Methional, 4 mM NADH. The dotted trace corresponds to an MHA standard with defined concentration.

Figure 3B:
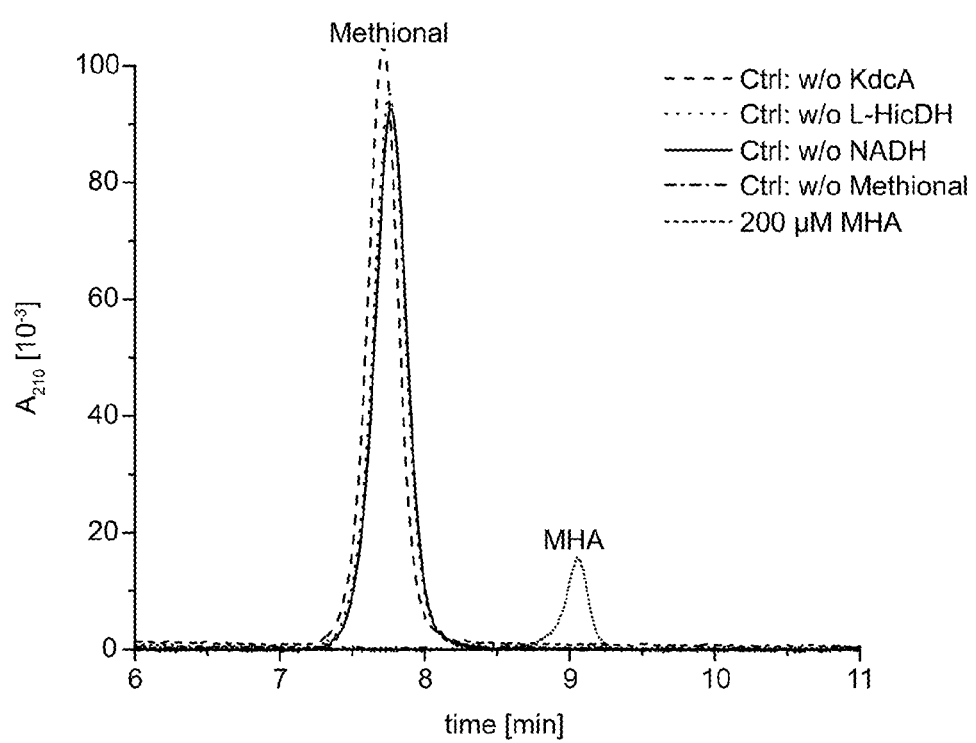

FIG. 3b: Control reactions under the same conditions as in (a) but omitting KdcA, L-HicDH, methional or NADH, respectively.

EXAMPLES

Example 1: Production of Decarboxylase in E. coli

The gene for a pyruvate decarboxylase (Pdc1; SEQ ID NO: 1; P06169; Killenberg-Jabs et al. (1997) Biochemistry 36, 1900-1905) and a phenylpyruvate decarboxylase (Aro10; SEQ ID NO: 3; Q06408; Kneen et al. (2011) FEBS J. 278, 1842-1853), both from *Saccharomyces cerevisiae*, as well as the gene for a branched chain decarboxylase (KdcA) from *Lactococcus lactis* (SEQ ID NO: 5; Q6QBS4; Yep et al. (2006) Bioorg. Chem. 34, 325-336) were synthesized with optimal codon usage for expression in E. coli (Geneart, Regensburg, Germany) and subsequently cloned on the expression vector pET21 (Novagen, Madison, Wis.) using the restriction enzymes NdeI and XhoI. The three resulting expression plasmids pET21-Pdc1, pET21-Aro10 and pET21-KdcA, respectively, which also encoded a carboxy-terminal $His_6$-tag for each of the enzymes, were verified by DNA-sequencing of the cloned structural gene (Eurofins Genomics, Ebersberg, Germany).

After chemical transformation of E. coli BL21 cells (Studier and Moffatt (1986) J. Mol. Biol. 189, 113-130) according to the $CaCl_2$-method (Sambrook et al. (1989) Molecular Cloning: A Laboratory Manual. Cold Spring Harbor Laboratory Press) with these expression plasmids, Pdc1 (SEQ ID NO: 2), Aro10 (SEQ ID NO: 4) and KdcA (SEQ ID NO: 6) were individually produced under control of the T7 promoter (Studier and Moffatt (1986) J Mol Biol 189, 113-130). To this end, bacteria were grown in 2 liter cultures in LB medium supplemented with 100 µg/ml ampicillin at 30° C. upon shaking until an $OD_{550}$ of 0.3-0.4 was reached. After reduction of the temperature during 45-60 min to 22° C., recombinant gene expression was induced at $OD_{550}$=0.6-0.8 for 5 h at 22° C. by addition of 0.01 mM isopropyl$^\beta$-D-1-thiogalactopyranoside (IPTG). Finally, the bacteria were harvested by centrifugation (10 min, 6000 rpm, fixed angle rotor, 4° C.) and the cell paste was frozen at −20° C.

All decarboxylases were purified using a two-step strategy comprising an immobilized metal ion affinity chromatography (IMAC) followed by a size exclusion chromatography (SEC). Therefore, the cells were resuspended in 3 ml 300 mM NaCl, 1 mM $MgSO_4$, 0.1 mM thiamine pyrophosphate (ThDP), 20 mM PIPES/NaOH pH 7.0 per 1 g wet weight and then disrupted mechanically using a French pressure cell (SLM Aminco, Rochester, N.Y.). The homogenate was centrifuged (30 min, 18000 rpm, fixed angle rotor, 4° C.), and the complete supernatant was applied to a 5 ml bed volume HisTrap HP column (GE Healthcare, Munich, Germany) charged with Ni(II) ions using 300 mM NaCl, 1 mM $MgSO_4$, 0.1 mM ThDP, 20 mM PIPES/NaOH pH 7.0 as running buffer. The bound decarboxylase was eluted by a linear concentration gradient of 0 to 500 mM imidazole/HCl in running buffer. Main fractions containing the decarboxylase were identified by Commassie-stained SDS-PAGE and concentrated to a final volume of 2-2.5 ml using a centrifugal filter unit with a nominal molecular weight limit (NMWL) of 30 kDa (Merck, Darmstadt, Germany). The concentrated sample was further purified via SEC using a 120 ml bed volume HiLoad Superdex 200 16/60 column (GE Healthcare) in the presence of 500 mM NaCl, 1 mM $MgSO_4$, 0.5 mM ThDP, 20 mM PIPES/NaOH pH 7.0.

As result, all three decarboxylases were obtained with >90% purity as confirmed by Commassie-stained SDS-PAGE analysis. The yield was approximately 50 mg, 10 mg and 30 mg per 1 liter culture volume for Pdc1, Aro10 and KdcA, respectively.

Example 2: Production of Alcohol Dehydrogenase in E. coli

The gene for a D-hydroxyisocaproate dehydrogenase (D-HicDH) from *Lactobacillus casei* (SEQ ID NO: 7; P17584; Hummel et al. (1985) Appl. Microbiol. Biotechnol. 21, 7-15) was synthesized with optimal codon usage for expression in E. coli (Geneart) and cloned on the expression vector pASK-IBA35(+) (IBA, Gottingen, Germany) using the restriction enzymes KasI and HindIII. The resulting expression plasmid pASK-IBA35(+)-D-HicDH, also encoding an amino-terminal $His_6$-tag for the D-HicDH, was verified by DNA-sequencing of the cloned structural gene (Eurofins Genomics). The gene for a L-hydroxyisocaproate dehydrogenase (L-HicDH) from *Lactobacillus confusus* (SEQ ID NO: 9; P14295; Schütte et al. (1984) Appl. Microbiol. Biotechnol. 19, 167-176) was synthesized with optimal codon usage for expression in E. coli (Geneart). As an amino-terminal $His_6$-tag would disrupt the tetramer formation of L-HicDH, the synthesized gene (SEQ ID NO: 9) was cloned on the expression vector pASK75(T7RBS)his using the restriction enzymes NdeI and Eco47III. The resulting expression plasmid pASK75(T7RBS)L-HicDH-his, encoding the L-HicDH with a carboxy-terminal $His_6$-tag, was verified by DNA-sequencing of the cloned structural gene (Eurofins Genomics).

Both enzymes, the D-HicDH (SEQ ID NO: 8) and the L-HicDH (SEQ ID NO: 10), were produced in *E. coli* BL21 under the control of the tet promoter (Skerra (1994) Gene 151, 131-135). Therefore, *E. coli* BL21 cells were transformed according to the $CaCl_2$-method (Sambrook et al., ibid.) with the corresponding expression plasmid and subsequently grown in 2l LB medium supplemented with 100 µg/ml ampicillin at 30° C. upon shaking until an $OD_{550}$=0.3-0.4 was reached. Then, for production of the D-HicDH the temperature was reduced to 22° C. during 45-60 min, while for the production of the L-HicDH the temperature was kept at 30° C. In both cases, the recombinant gene expression was induced with 0.2 mg/l anhydrotetracycline (aTc; Acros, Geel, Belgium) at $OD_{550}$=0.6-0.8. After 5 h at 22° C./30° C. the bacteria were harvested by centrifugation (10 min, 6000 rpm, fixed angle rotor, 4° C.) and frozen at −20° C.

To purify both dehydrogenases, the cells containing the D-HicDH were resuspended in 3 ml 150 mM NaCl, 50 mM PIPES pH 7.0 per 1 g wet weight while the cells containing L-HicDH were resuspended in 3 ml 300 mM NaCl, 50 mM $KP_i$ pH 7 per 1 g wet weight. Then the bacteria were disrupted mechanically in a French pressure cell. The homogenate was centrifuged (30 min, 18000 rpm, fixed angle rotor, 4° C.) and the entire supernatant was applied to a 5 ml bed volume HisTrap HP column charged with Ni(II) ions using 150 mM NaCl, 50 mM PIPES pH 7.0 for the D-HicDH and 300 mM NaCl, 50 mM $KP_i$ pH 7 for the L-HicDH, respectively, as running buffer. The bound dehydrogenase was eluted by a linear concentration gradient of 0 to 500 mM imidazole/HCl in running buffer. Main fractions containing the dehydrogenase were identified by Commassie-stained SDS-PAGE and concentrated to a final volume of 4-5 ml using a centrifugal filter unit with a NMWL of 30 kDa. In a second step the concentrated sample was purified by SEC using a 320 ml bed volume HiLoad Superdex 200 26/60 column in the presence of 150 mM NaCl, 50 mM PIPES pH 7.0 and 300 mM NaCl, 20 mM $KP_i$ pH 6.5 for D-HicDH and L-HicDH, respectively.

Both alcohol dehydrogenases were obtained with >90% purity as confirmed by SDS-PAGE analysis with a yield of 7 mg/l for D-HicDH and >47 mg/l for L-HicDH.

Example 3: Production of Formate Dehydrogenase in *E. coli*

The gene for the formate dehydrogenase from *Pseudomonas* sp. 101 (PseFDH; SEQ ID NO: 11; P33160; Egorov et al. (1979) Eur. J. Biochem. 99, 569-576) was synthesized with optimal codon usage for expression in *E. coli* (Geneart) and cloned on the expression vector pASK-IBA35(+) using the restriction enzymes KasI and HindIII. Also, the gene for the formate dehydrogenase from *Candida boidinii* (CboFDH; 013437; Schütte et al. (1976) Eur. J. Biochem. 62, 151-160) was synthesized with optimal codon usage for expression in *E. coli* (Geneart) carrying two amino acid exchanges, C23A and F285S, to potentially enhance stability and activity. Substitution of Cys23 with its reactive thiol side chain by Ala should stabilize the enzyme against oxidation in a similar manner as the previously described mutation C23S (Slusarczyk et al. (2000) Eur. J. Biochem, 267, 1280-1287). The substitution of Phe285 by Ser was previously shown to enhance the enzyme activity (Felber (2001) Doctoral Thesis, Heinrich-Heine University Dusseldorf; US 20030157664 A1). The resulting gene coding for CboFDH(C23A/F285S) (SEQ ID NO: 13) was cloned on pASK-IBA35(+) as described above for the PseFDH. The resulting expression plasmids pASK-IBA35(+)-CboFDH and pASK-IBA35(+)-PseFDH, respectively, both also encoding an amino-terminal $His_6$-tag, were verified by DNA-sequencing of the cloned structural gene (Eurofins Genomics).

PseFDH (SEQ ID NO: 12) as well as CboFDH(C23A/F285S) (SEQ ID NO: 14) were produced in *E. coli* BL21 under the same conditions as the alcohol dehydrogenase D-HicDH described herein above in Example 2.

For the purification of both FDHs the bacterial paste was resuspended in 3 ml per 1 g wet cell mass in 300 mM NaCl, 50 mM $KP_i$ pH 7.5 and disrupted mechanically using a French pressure cell. After centrifugation (30 min, 18000 rpm, fixed angle rotor, 4° C.), the entire supernatant was applied to a 5 ml bed volume HisTrap HP column charged with Ni(II) ions using 300 mM NaCl, 50 mM $KP_i$ pH 7.5 as running buffer. The bound FDH was eluted by a linear concentration gradient of 0 to 500 mM imidazole/HCl in running buffer. The eluted protein was concentrated using a centrifugal filter unit with a NMWL of 30 kDa. 4 ml protein solution containing approximately 50 mg PseFDH, or 6 ml containing about 130 mg CboFDH(C23A/F285S), were loaded on a 320 ml bed volume HiLoad Superdex 200 26/60 column for SEC in the presence of 300 mM NaCl, 20 mM $KP_i$ pH 7.5.

The formate dehydrogenases PseFDH and CboFDH (C23A/F285S) were obtained in yields of 19 mg/l and 45 mg/l, respectively. High purity of >95% was confirmed by Commassie-stained SDS-PAGE analysis.

Figure 1:
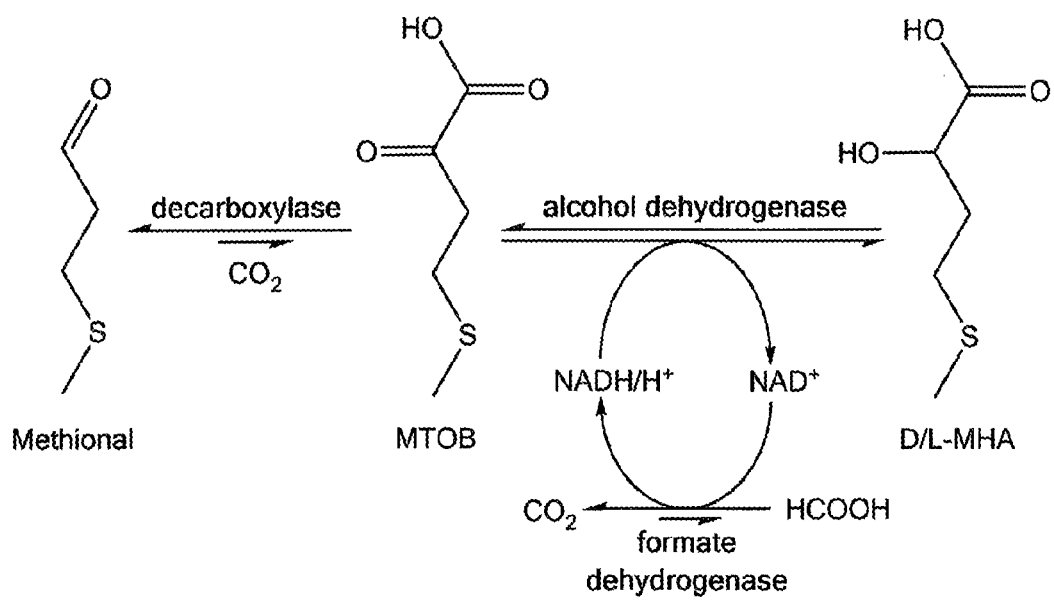
FIG. 1: Scheme for the two-step biocatalytic synthesis of a methionine-hydroxy-analog (MHA) from 3-(methylthio-propanal (methional) in the presence of a decarboxylase, an alcohol dehydrogenase and optionally a formate dehydrogenase as a biocatalytic NADH regeneration system.

Example 4: Synthesis of the D-Methionine-Hydroxy-Analog (D-MHA) from 3-(Methylthio)Propanal (Methional) by a Two-Step Biocatalytic Reaction Involving a Decarboxylase and an Alcohol Dehydrogenase To synthesize D-MHA in the proposed two-step biocatalytic reaction (FIG. 1), the purified decarboxylase KdcA and the alcohol dehydrogenase D-HicDH were mixed with the following reagents in a 10 ml pressure reactor (Tinyclave steel; Biichi, Uster, Switzerland) to a final volume of 1 ml:

| Reagent/enzyme | Final concentration |
| --- | --- |
| $NaHCO_3$ | 200 mM |
| ThDP | 0.5 mM |
| $MgCl_2$ | 1 mM |
| KdcA | 10 µM |
| D-HicDH | 1 µM |
| NADH | 2 mM |
| Methional | 4 mM |

The carboxylation reaction under catalysis of the decarboxylase KdcA was started by the addition of the substrate methional and application of 200 kPa (2 bar) $CO_2$. The initial pH of the mixture was 8, which shifted to ca. 6.5 upon application of $CO_2$ (as measured with a fixed-color-pH indicator stick (Carl Roth, Karlsruhe, Germany) in a sample). After 1 h incubation the mixture was recovered from the reactor and centrifuged for 5 min at 13400 rpm in a bench top centrifuge to remove precipitated proteins. In the clear supernatant, product formation was analyzed by HPLC using a C18 column (Gemini C18, 4.6×15 mm, 3 µm, 110 A; Phenomenex, Aschaffenburg, Germany) with isocratic elution in 4% (v/v) aqueous acetonitrile supplemented with 1% (v/v) phosphoric acid.

Compared to control reactions with omission of KdcA, D-HicDH, methional or NADH, respectively (FIG. 2b), the chromatograms of the two-step biocatalytic synthesis in the presence of the decarboxylase (e.g. KdcA) and the dehydrogenase (e.g. D-HicDH) clearly demonstrated that D-MHA was produced from methional under the chosen reaction conditions (FIG. 2a). By elongating the reaction time to 8 h, increasing the $CO_2$ pressure to 800 kPa (8 bar) and doubling the KdcA concentration to 20 µM the D-MHA yield was improved from 3% to 23% (FIG. 2c).

Example 5: Synthesis of D-MHA from Methional by a Two-Step Biocatalytic Reaction Involving a Decarboxylase and an Alcohol Dehydrogenase in the Presence of a Biocatalytic NADH Regeneration System During the two-step enzymatic synthesis of D-MHA from methional catalyzed by a decarboxylase (e.g. KdcA) and an alcohol dehydrogenase (e.g. D-HicDH) the cosubstrate NADH is consumed by the dehydrogenase for reduction of the α-carbonyl group of MTOB. In order to recycle NADH from its oxidized form $NAD^+$ in situ a formate dehydrogenase (e.g. CboFDH(C23A/F285S)) can be employed. This enzyme oxidizes formate with $NAD^+$ as cosubstrate to yield $CO_2$, which may also serve as substrate for the carboxylation reaction of methional, as well as NADH (Schütte et al. (1976) Eur. J. Biochem. 62, 151-160; Wichmann et al. (1981) Biotechnol. Bioeng. 23, 2789-2802).

This three-enzyme coupled reaction was performed under a limiting concentration of NADH (80 µM), which was added to a reaction mixture in a 10 ml pressure reactor (Tinyclave steel) containing the following reagents in a final volume of 1 ml:

| Reagent/enzyme | Final concentration |
| --- | --- |
| NaHCO$_3$ | 200 mM |
| ThDP | 0.5 mM |
| MgCl$_2$ | 1 mM |
| KdcA | 10 µM |
| D-HicDH | 0.5 µM |
| CboFDH(C23A/F285S) | 10 µM |
| NADH | 80 µM |
| NaHCO$_3$ | 25 mM |
| Methional | 4 mM |

As in Example 4 the reaction was started by the addition of methional and application of 800 kPa (8 bar) $CO_2$. The initial pH of the mixture was 8 and shifted to ca. 6.5 upon application of $CO_2$ (as measured with a fixed-color-pH indicator stick in a sample). After 1.5 h incubation, the mixture was recovered from the reactor and analyzed using HPLC as described in Example 4. The resulting chromatogram showed a significantly increased D-MHA peak (~114 µM) compared to the control reaction (~38 µM) in which the substrate formate of the formate dehydrogenase was omitted (FIG. 2 D).

Thus, the addition of a formate dehydrogenase together with its substrate to the D-MHA-forming reaction, involving a decarboxylase (e.g., KdcA) and a NADH dependent alcohol dehydrogenase (e.g. D-HicDH), can compensate for limiting NADH concentrations and regenerate this cosubstrate.

Example 6: Synthesis of the L-Methionine-Hydroxy-Analog (L-MHA) from Methional by a Two-Step Biocatalytic Reaction Involving a Decarboxylase and an Alcohol Dehydrogenase To synthesize L-MHA in the proposed two-step biocatalytic reaction (FIG. 1), the purified decarboxylase (e.g. KdcA) and the alcohol dehydrogenase (e.g. L-HicDH) were mixed with the following reagents in a 10 ml pressure reactor (Tinyclave steel) to a final volume of 1 ml:

| Reagent/enzyme | Final concentration |
| --- | --- |
| NaHCO$_3$ | 200 mM |
| ThDP | 0.5 mM |
| MgCl$_2$ | 1 mM |
| KdcA | 20 µM |
| L-HicDH | 500 nM |
| NADH | 4 mM |
| Methional | 4 mM |

The reaction was started by the addition of methional and application of 800 kPa (8 bar) $CO_2$ as described herein above in Examples 4 and 5. Upon the application of $CO_2$ the initial pH of 8 was shifted to 6.5 as measured with a fixed-color-pH indicator stick in a sample.

After 45 min at 800 kPa (8 bar), the mixture was recovered from the autoclave and centrifuged for 5 min at 13400 rpm in a bench top centrifuge to remove precipitated proteins. In the cleared supernatant, product formation was analyzed by HPLC using a C18 column as described in Example 4.

The chromatograms for the two-step biocatalytic synthesis of L-MHA from methional via combined action of a decarboxylase (e.g. KdcA) and a dehydrogenase (e.g. L-HicDH; FIG. 3 A) and for control reactions with KdcA, L-HicDH, methional or NADH, respectively, omitted (FIG. 3 B) clearly demonstrated that L-MHA was specifically synthesized from methional under the chosen reaction conditions only if both enzymes, a decarboxylase, e.g. KdcA, and an alcohol dehydrogenase, e.g. L-HicDH, as well as the cofactor NADH were present.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A method for producing D- or L-2-hydroxy-4-methylmercaptobutanoic acid (MHA), comprising reacting a mixture comprising: 3-(methylthio)-propanal (methional); carbon dioxide; a decarboxylase (EC 4.1.1); a corresponding cofactor of the decarboxylase; an alcohol dehydrogenase (EC 1.1.1); and NADH or NADPH, to form D- or L-2-hydroxy-4-methylmercaptobutanoic acid (MHA) or a salt thereof.

2. The method of claim 1, wherein the cofactor comprises thiamine pyrophosphate.

3. The method of claim 1, wherein the decarboxylase is selected from the group consisting of pyruvate decarboxylase Pdc1, which originates from *Saccharomyces cerevisiae*, phenylpyruvate decarboxylase Aro10, which originates from *Saccharomyces cerevisiae*, and branched chain decarboxylase KdcA, which originates from *Lactococcus lactis*.

4. The method of claim 1, wherein said method is for producing D-2-hydroxy-4-methylmercapto-butanoic acid (D-MHA), and wherein the alcohol dehydrogenase is a D-hydroxyisocaproate dehydrogenase.

5. The method of claim 4, wherein the D-hydroxyisocaproate dehydrogenase is D-HicDH from *Lactobacillus casei*.

6. The method of claim 1, where said method is for producing L-2-hydroxy-4-methylmercapto-butanoic acid (L-MHA), and wherein the alcohol dehydrogenase is a L-hydroxyisocaproate dehydrogenase.

7. The method of claim 6, wherein the L-hydroxyisocaproate dehydrogenase is L-HicDH from *Lactobacillus confusus*.

8. The method of claim 1, wherein the carbon dioxide is applied to the mixture at a pressure from 10 to 7400 kPa.

9. The method of claim 1, wherein the mixture further comprises formic acid or a salt thereof and a formate dehydrogenase (EC 1.17.1.9).

10. The method of claim 9, wherein the formate dehydrogenase is selected from the group consisting of a formate dehydrogenase from *Pseudomonas* sp. and a formate dehydrogenase from *Candida* sp.

11. The method of claim 2, wherein the decarboxylase is selected from the group consisting of pyruvate decarboxylase Pdc1, which originates from *Saccharomyces cerevisiae*, phenylpyruvate decarboxylase Aro10, which originates from *Saccharomyces cerevisiae*, and branched chain decarboxylase KdcA, which originates from *Lactococcus lactis*.

12. The method of claim 11, wherein said method is for producing D-2-hydroxy-4-methylmercapto-butanoic acid (D-MHA), and wherein the alcohol dehydrogenase is a D-hydroxyisocaproate dehydrogenase.

13. The method of claim 12, wherein the D-hydroxyisocaproate dehydrogenase is D-HicDH from *Lactobacillus casei*.

14. The method of claim 13, wherein the carbon dioxide is applied to the mixture at a pressure from 10 to 7400 kPa.

15. The method of claim 14, wherein the mixture further comprises formic acid or a salt thereof and a formate dehydrogenase (EC 1.17.1.9).

16. The method of claim 15, wherein the formate dehydrogenase is selected from the group consisting of a formate dehydrogenase from *Pseudomonas* sp. and a formate dehydrogenase from *Candida* sp.

17. The method of claim 2, where said method is for producing L-2-hydroxy-4-methylmercapto-butanoic acid (L-MHA), and wherein the alcohol dehydrogenase is a L-hydroxyisocaproate dehydrogenase.

18. The method of claim 17, wherein the L-hydroxyisocaproate dehydrogenase is L-HicDH from *Lactobacillus confusus*.

19. The method of claim 18, wherein the decarboxylase is selected from the group consisting of pyruvate decarboxylase Pdc1, which originates from *Saccharomyces cerevisiae*, phenylpyruvate decarboxylase Aro10, which originates from *Saccharomyces cerevisiae*, and branched chain decarboxylase KdcA, which originates from *Lactococcus lactis*.

20. The method of claim 19, wherein the carbon dioxide is applied to the mixture at a pressure from 10 to 7400 kPa and wherein the mixture further comprises formic acid or a salt thereof and a formate dehydrogenase (EC 1.17.1.9).

* * * * *